(12) United States Patent
Gong et al.

(10) Patent No.: US 8,962,675 B1
(45) Date of Patent: Feb. 24, 2015

(54) ATRASENTAN MANDELATE SALTS

(71) Applicant: AbbVie Inc., North Chicago, IL (US)

(72) Inventors: Yuchuan Gong, Waukegan, IL (US); Geoff G. Zhang, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/133,297

(22) Filed: Dec. 18, 2013

Related U.S. Application Data

(60) Provisional application No. 61/877,101, filed on Sep. 12, 2013.

(51) Int. Cl.
*A61K 31/519* (2006.01)
*C07D 405/04* (2006.01)
*C07C 59/54* (2006.01)

(52) U.S. Cl.
CPC .............. *C07D 405/04* (2013.01); *C07C 59/54* (2013.01)
USPC ........................................................ 514/422

(58) Field of Classification Search
CPC .............. A61K 31/5377; A61K 31/519; C07D 471/04; C07D 487/04
USPC ..................... 514/248, 253.04, 422
See application file for complete search history.

(56) References Cited

U.S. PATENT DOCUMENTS

| 5,622,971 | A | 4/1997 | Winn et al. |
| 5,731,434 | A | 3/1998 | Winn et al. |
| 5,767,144 | A | 6/1998 | Winn et al. |
| 5,801,250 | A | 9/1998 | Oliver-Shaffer et al. |
| 6,124,341 | A | 9/2000 | Tasker et al. |
| 6,162,927 | A | 12/2000 | Winn et al. |
| 6,329,536 | B1 | 12/2001 | Ji et al. |
| 6,380,241 | B1 | 4/2002 | Winn et al. |
| 6,462,194 | B1 | 10/2002 | Winn et al. |
| 6,946,481 | B1 | 9/2005 | Winn et al. |
| 7,208,517 | B1 * | 4/2007 | Winn et al. .................... 514/422 |
| 7,297,709 | B2 | 11/2007 | Dai et al. |
| 7,365,093 | B2 | 4/2008 | Winn et al. |
| 7,598,283 | B2 | 10/2009 | Dai et al. |
| 8,063,091 | B2 | 11/2011 | Dai et al. |

(Continued)

FOREIGN PATENT DOCUMENTS

| WO | 9111172 A1 | 8/1991 |
| WO | 9402518 A1 | 2/1994 |

(Continued)

OTHER PUBLICATIONS

Dahlen et al (Acta Chemica Scandinavica 45 (1991) 200-205).*

(Continued)

*Primary Examiner* — Savitha Rao
*Assistant Examiner* — Angela Brown-Pettigrew

(57) ABSTRACT

The present disclosure relates to: (a) mandelate salts of atrasentan, (b) pharmaceutical compositions comprising an atrasentan mandelate salt, and, optionally, one or more additional therapeutic agents; (b) methods of using an atrasentan mandelate salt to treat nephropathy, chronic kidney disease, and/or other conditions; (c) kits comprising a first pharmaceutical composition comprising an atrasentan mandelate salt, and, optionally, a second pharmaceutical composition comprising one or more additional therapeutic agents; (d) methods for the preparation of an atrasentan mandelate salt; and (e) atrasentan mandelate salts prepared by such method.

11 Claims, 24 Drawing Sheets

Microscopic Image of Hemi-Sulfate Salt (1:1 Stoichiometry), Monohydrate

Microscopic Image of S-Mandelate Salt (1:1 Stoichiometry), Anhydrate

(56) References Cited

U.S. PATENT DOCUMENTS

| | | |
|---|---|---|
| 2002/0055457 A1 | 5/2002 | Janus et al. |
| 2003/0022811 A1 | 1/2003 | Singh et al. |
| 2003/0092757 A1 | 5/2003 | Singh et al. |
| 2005/0113306 A1 | 5/2005 | Janus et al. |
| 2005/0113307 A1 | 5/2005 | Janus et al. |
| 2006/0035867 A1 | 2/2006 | Janus et al. |
| 2007/0123582 A1 | 5/2007 | Zhang |
| 2008/0132710 A1 | 6/2008 | Henry et al. |
| 2010/0184026 A1 | 7/2010 | Lesniewski et al. |
| 2013/0030189 A1 | 1/2013 | Dai et al. |

FOREIGN PATENT DOCUMENTS

| | | |
|---|---|---|
| WO | 9855148 A1 | 12/1998 |
| WO | 2006034084 A1 | 3/2006 |
| WO | 2006034085 A1 | 3/2006 |
| WO | 2006034094 A1 | 3/2006 |
| WO | 2006034234 A1 | 3/2006 |

OTHER PUBLICATIONS

Berge et al.; "Pharmaceutical Salts"; 1997; Journal of Pharmaceutical Sciences; 66(1): 1-19.*

American Society for Testing and Materials (ASTM) Practice G31-72 "Standard Practice for Laboratory Immersion Corrosion Testing of Metals", vol. 3 (2), (Reapproved 2004).

IUPAC 1974 Recommendations for Section E, Fundamental Stereochemistry, Pure and Applied Chemistry, 1976, vol. 45, pp. 13-30.

Jenkins R., et al., "Introduction to XRay Powder Diffractometry," John Wiley & Sons, 1996.

Remington J.P., "Pharmaceutical Sciences", MACK Publishing Company, New Jersey, 1991.

Rowe R.C., et al., "Handbook of Pharmaceutical Excipients," 7th Edition, Pharmaceutical Press, 2012.

* cited by examiner

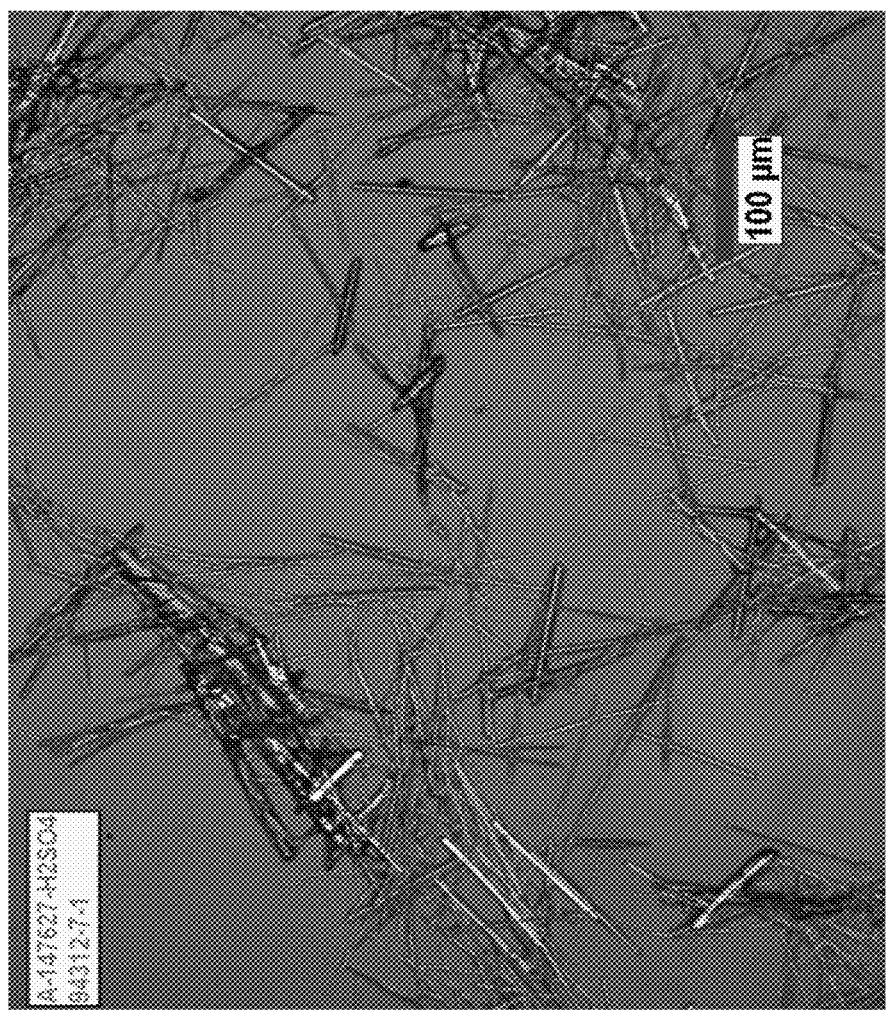
Figure 1-A:
Microscopic Image of Hemi-Sulfate Salt (1:1 Stoichiometry), Monohydrate

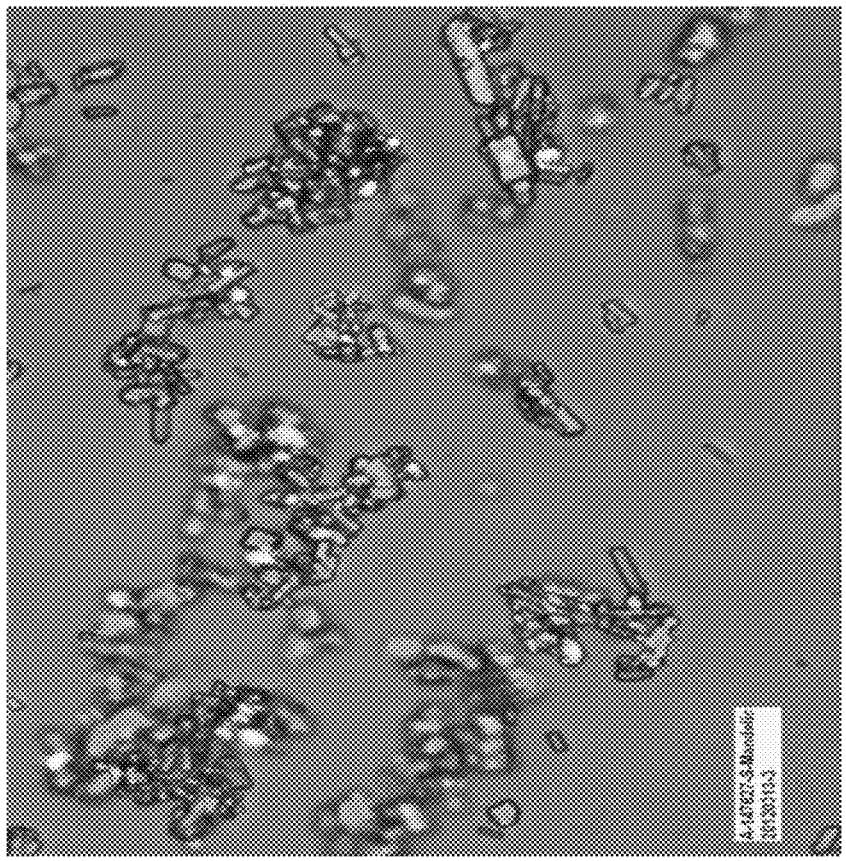
Figure 1-B:
Microscopic Image of S-Mandelate Salt (1:1 Stoichiometry), Anhydrate

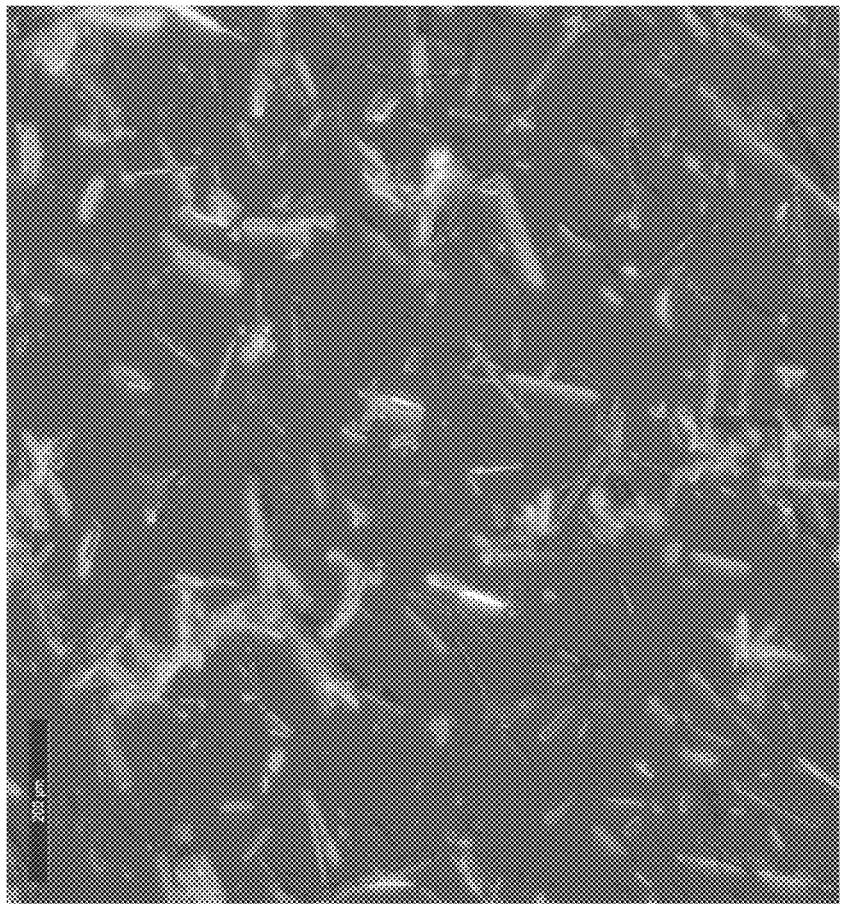
Figure 1-C:
Microscopic Image of Monohydrochloride Salt, Crystalline Form II

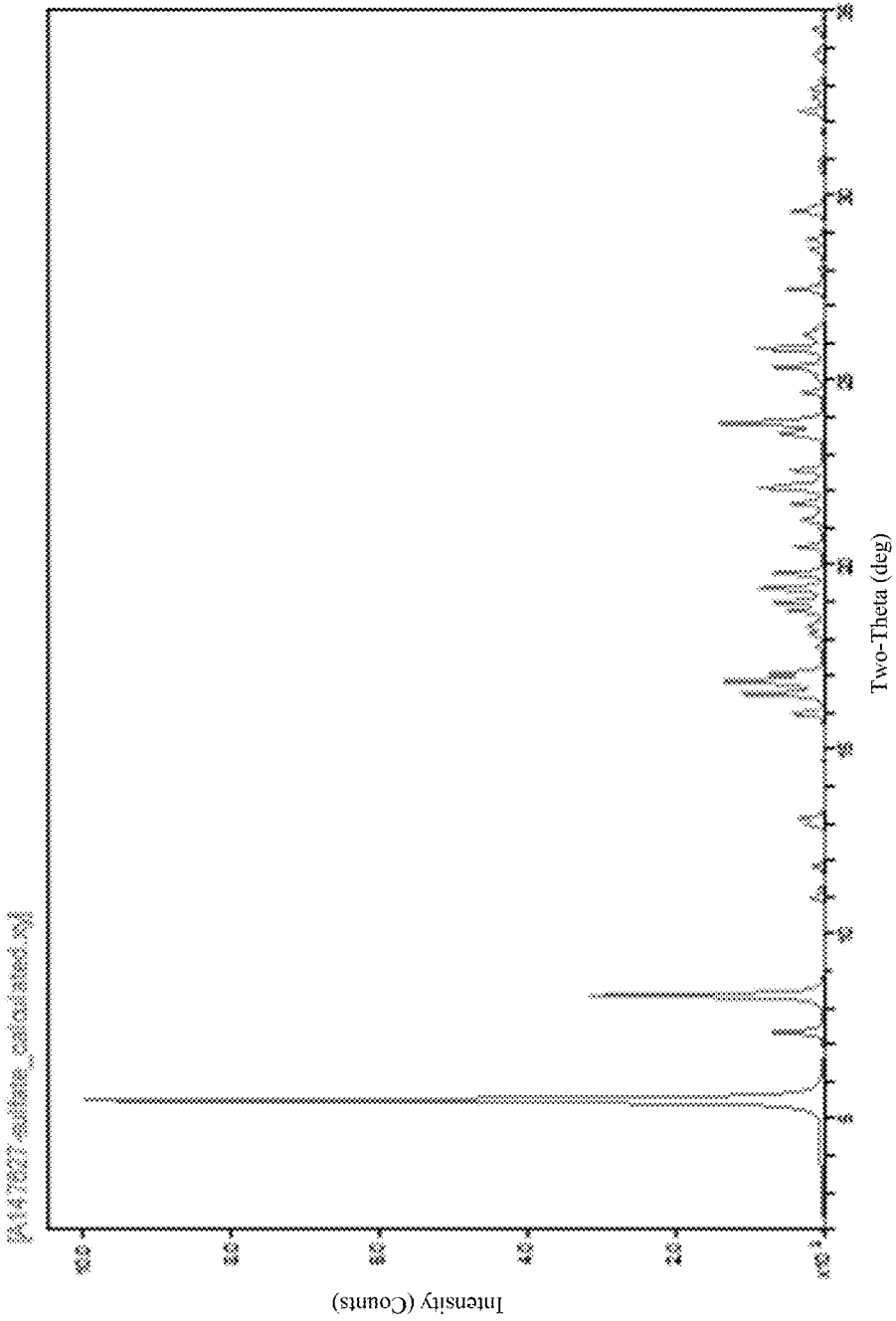
Figure 2-A:
PXRD Pattern of Hemi-Sulfate Salt (1:1 Stoichiometry), Monohydrate

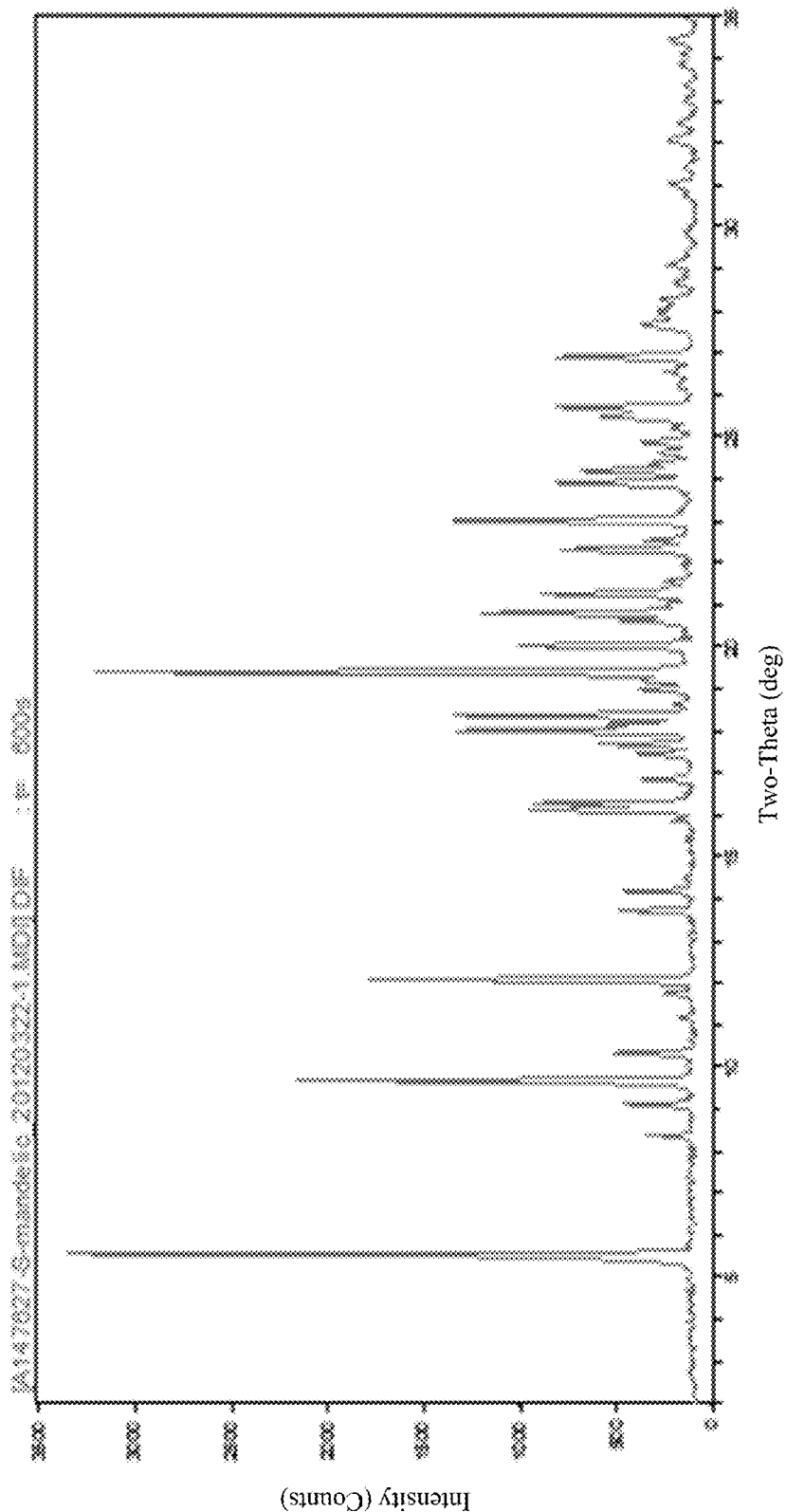

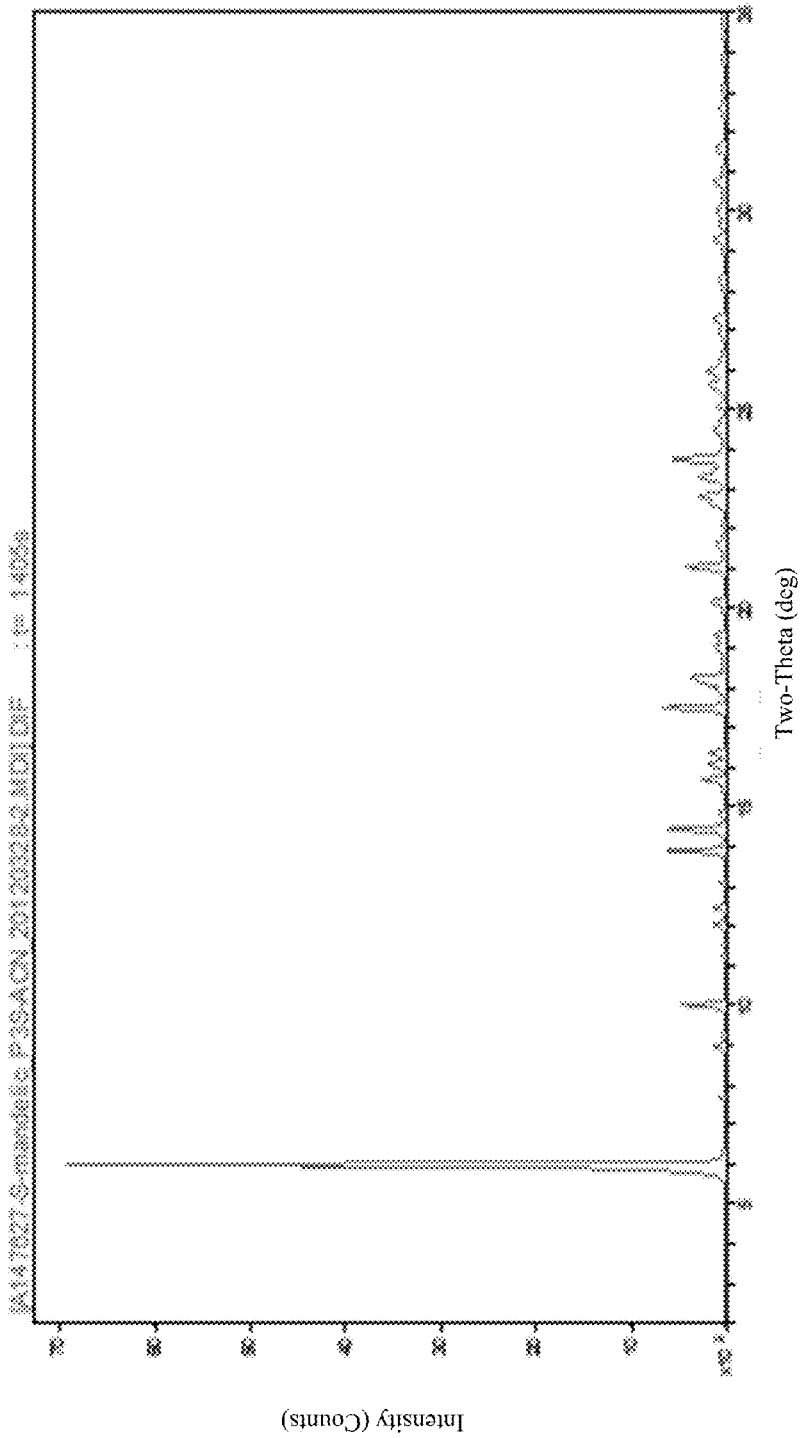

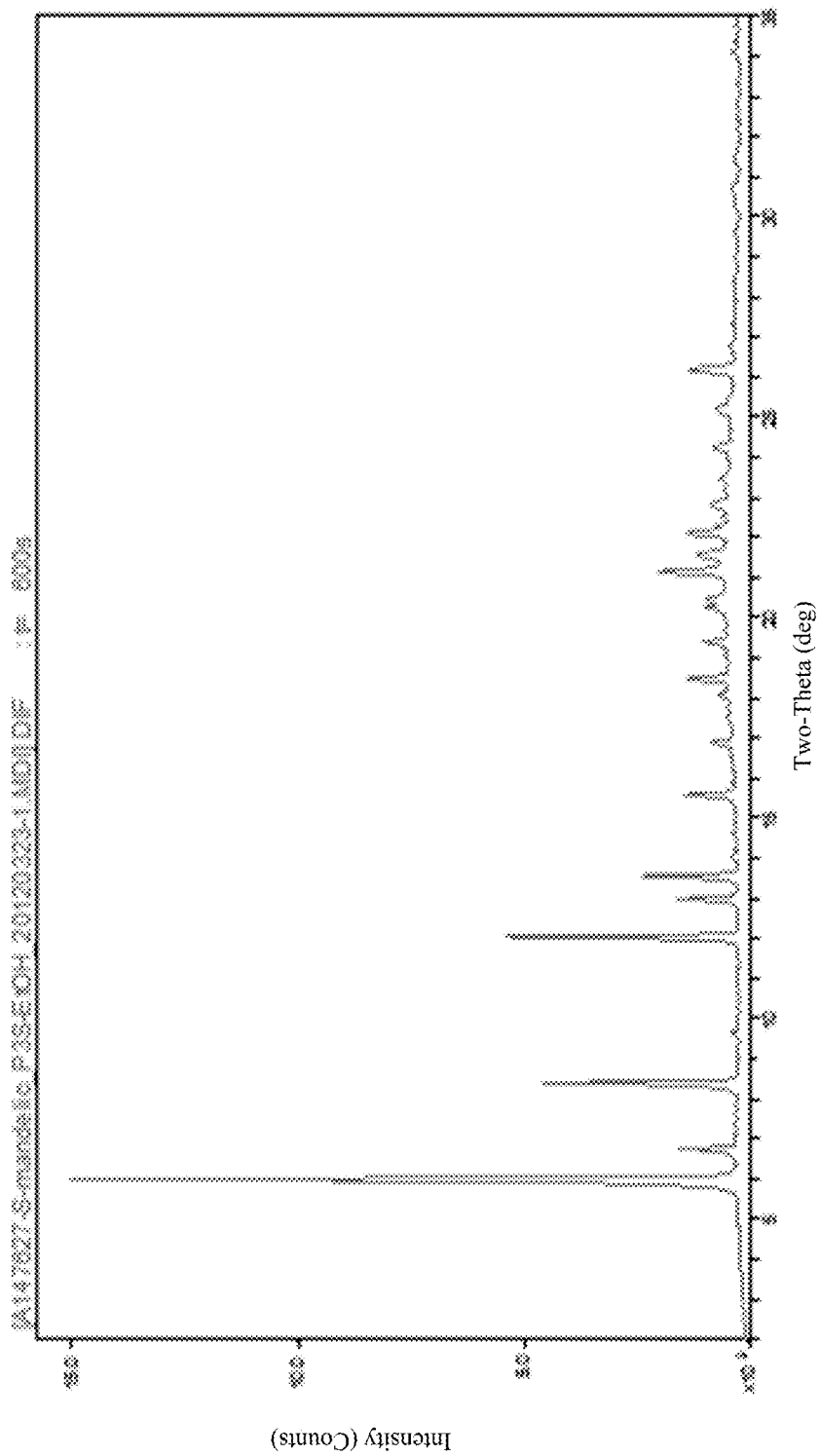
Figure 2-D:
PXRD Pattern of S-Mandelate Salt (1:1 Stoichiometry), Crystallized From Ethanol

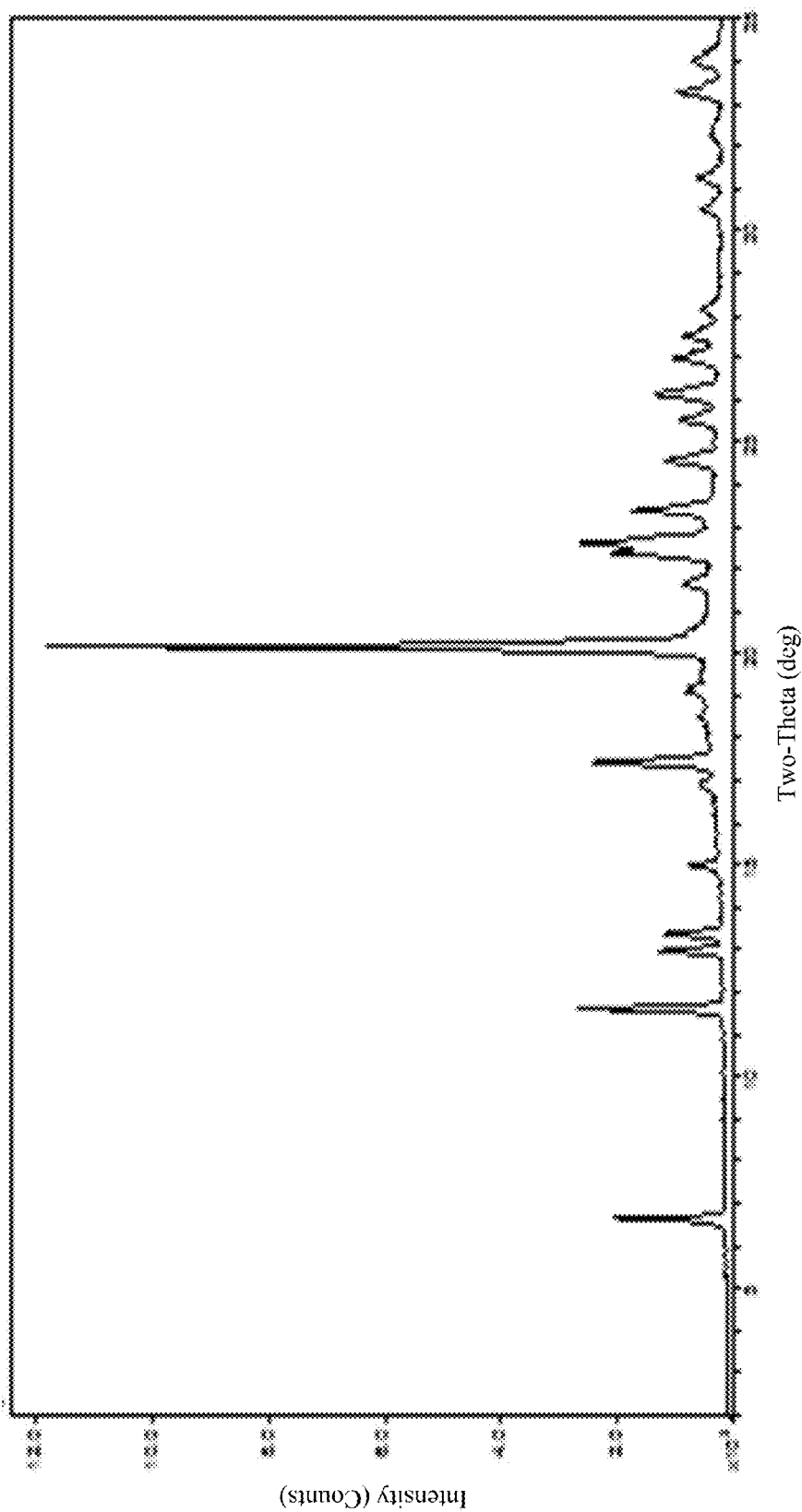
Figure 2-E:
PXRD Pattern of S-Mandelate Salt (1:1 Stoichiometry), Crystallized From Pyridine

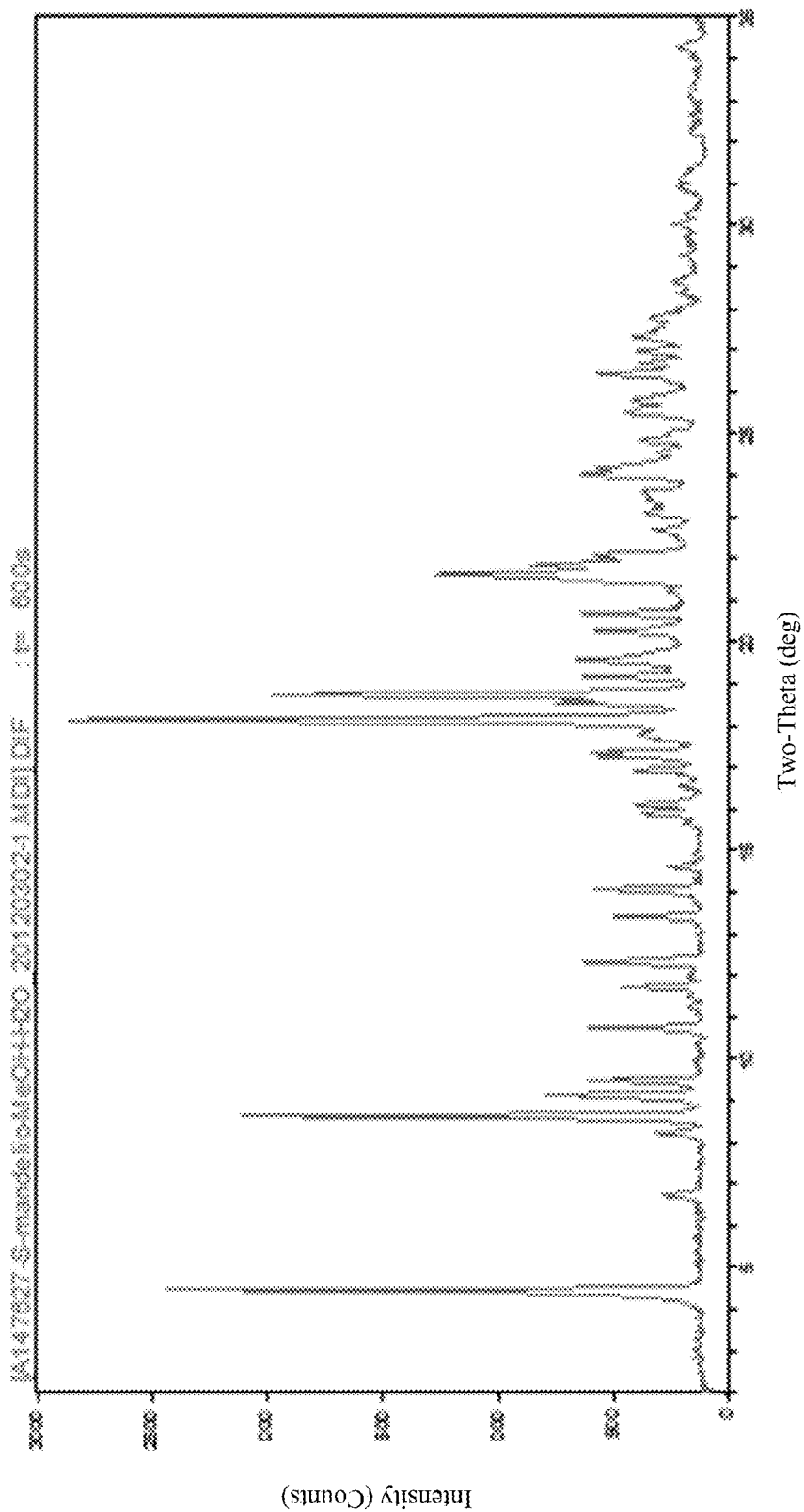
Figure 2-F:
PXRD Pattern of S-Mandelate Salt (2:1 Stoichiometry), Hydrate

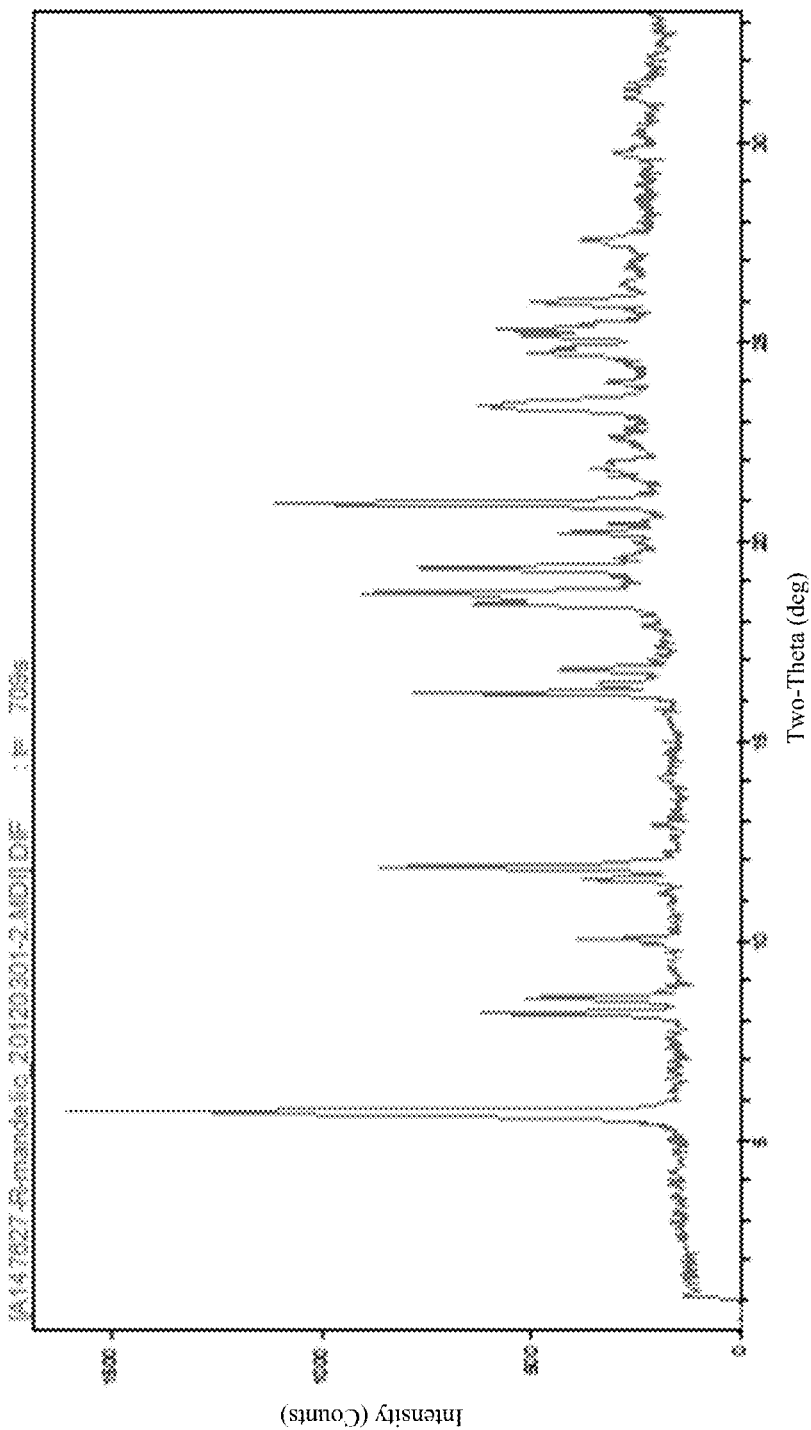
Figure 2-G:
PXRD Pattern of R-Mandelate Salt (1:1 Stoichiometry), Anhydrate

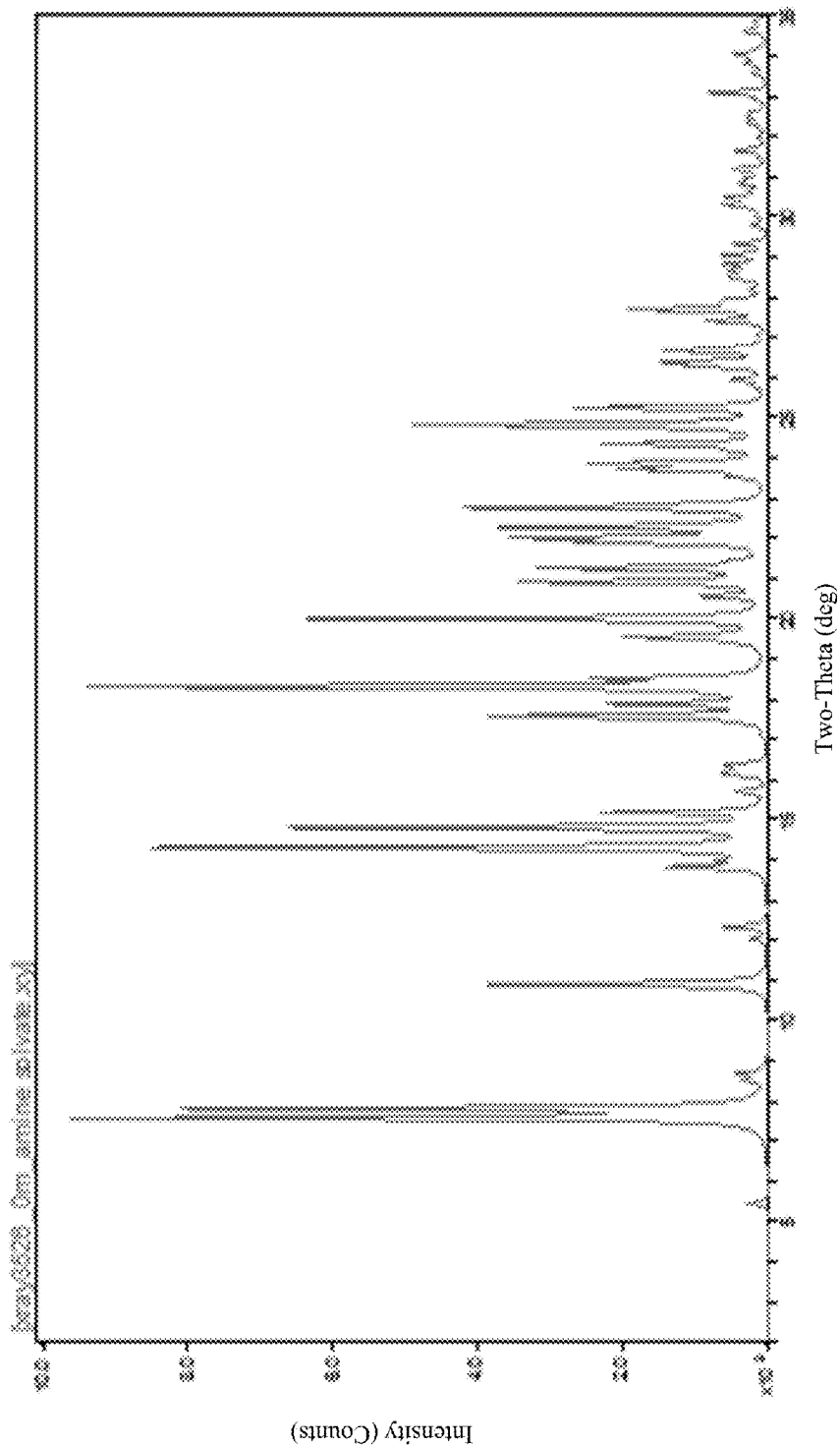
Figure 2-H:
Calculated PXRD Pattern of n-Butylamine Salt (1:1 Stoichiometry), Anhydrate

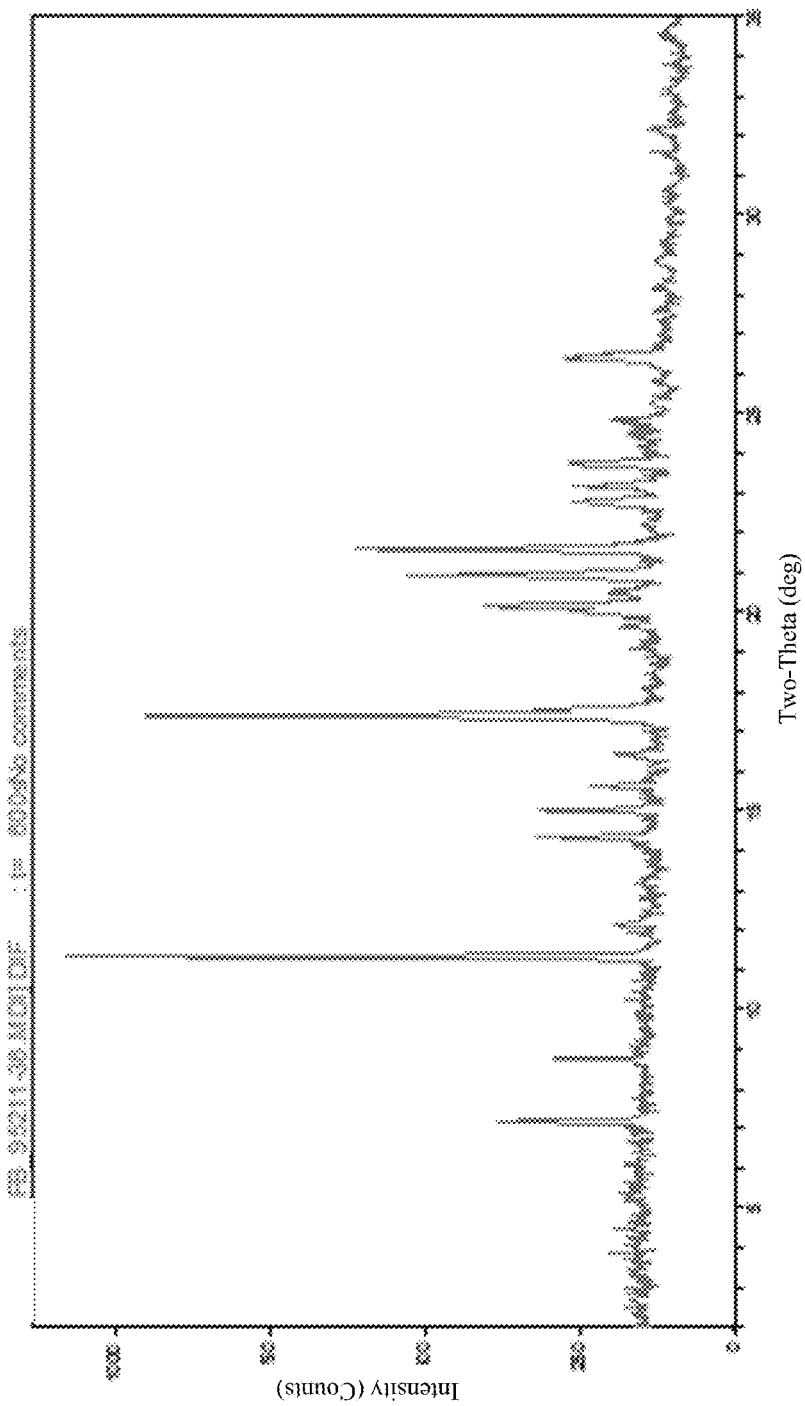
Figure 2-I:
PXRD Pattern of Parent, Anhydrate

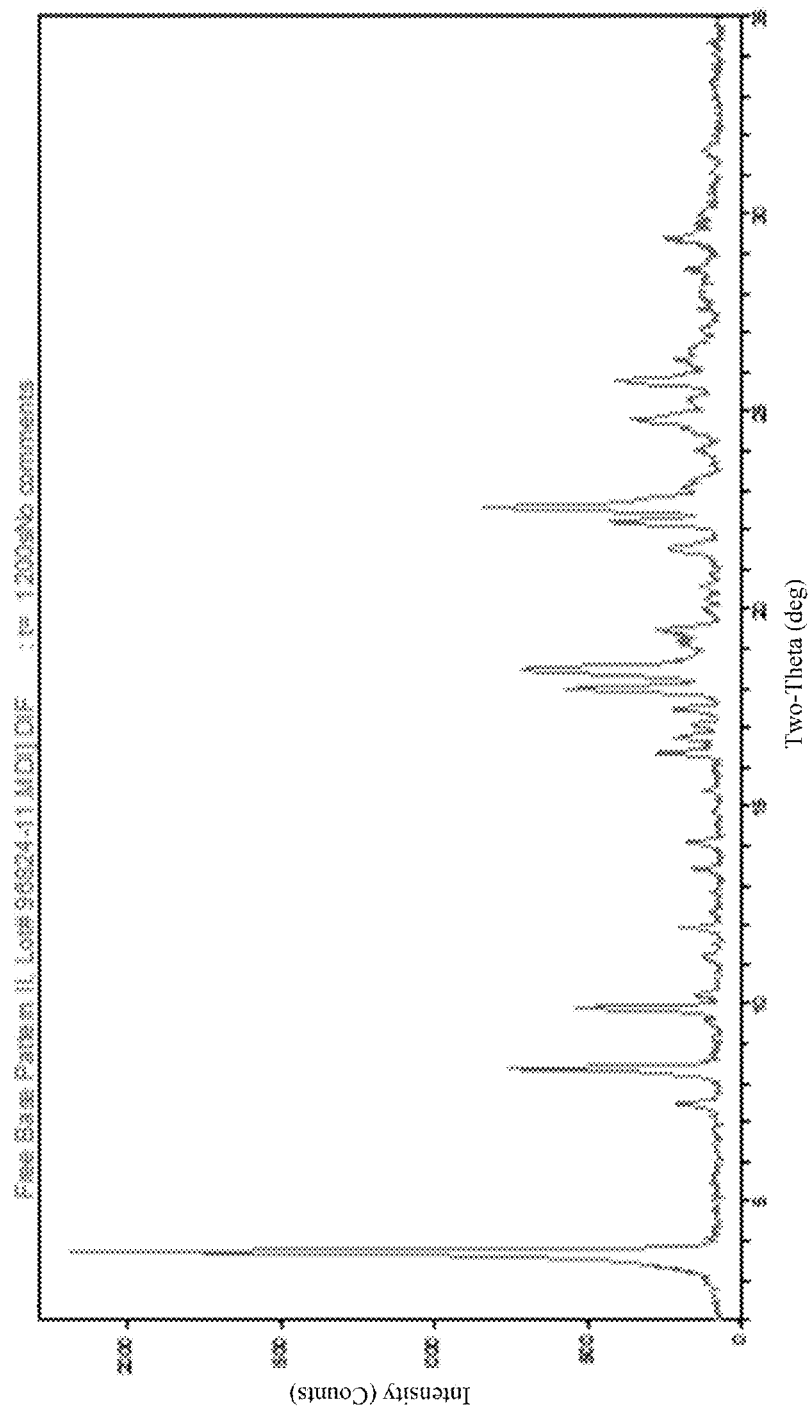
Figure 2-J:
PXRD Pattern of Parent, Quarter-Hydrate

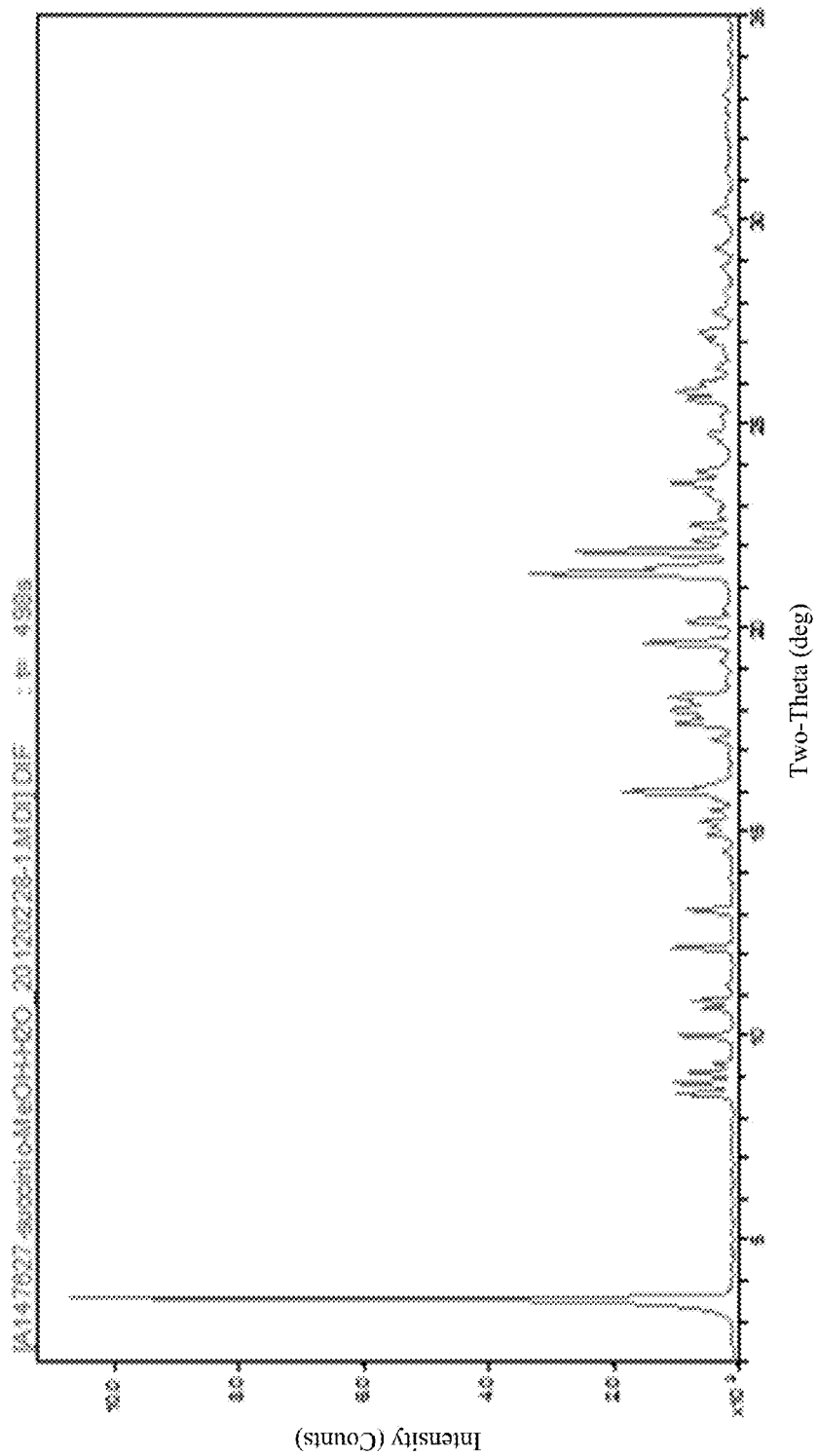
Figure 2-K:
PXRD Pattern of Parent, Hemi-Hydrate

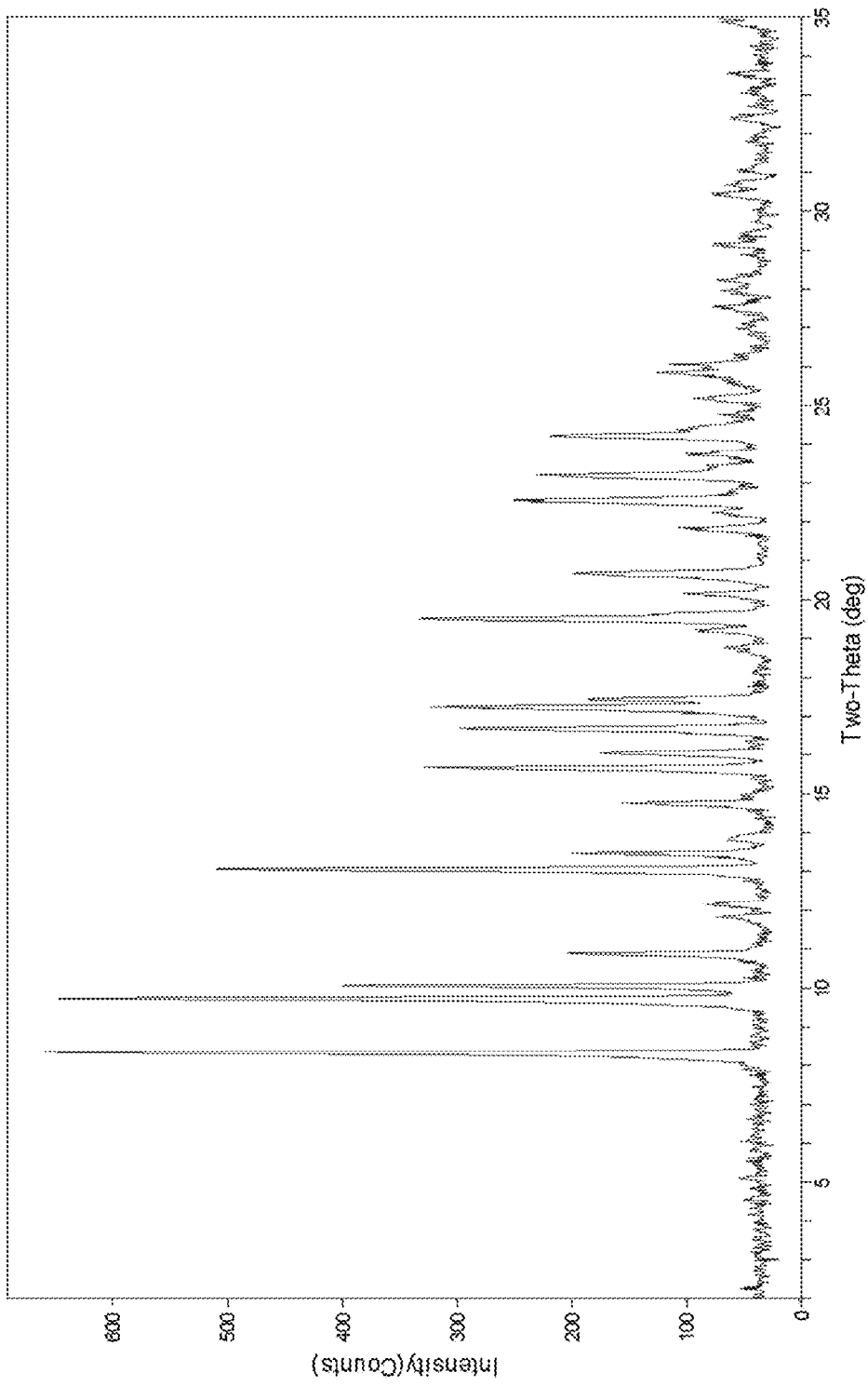
Figure 2-L:
PXRD Pattern of Monohydrochloride Salt, Crystalline Form I

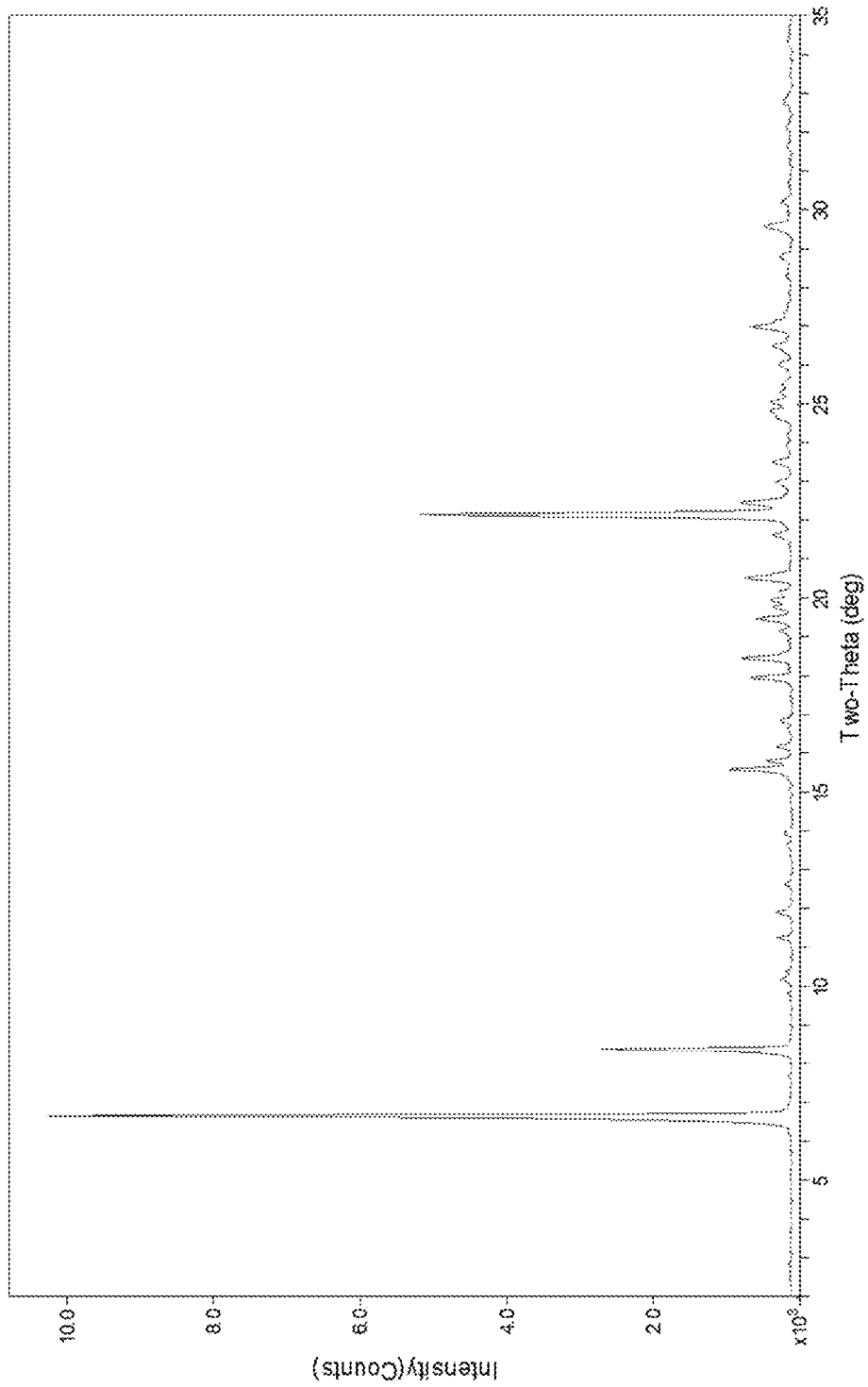
Figure 2-M:
PXRD Pattern of Monohydrochloride Salt, Crystalline Form II

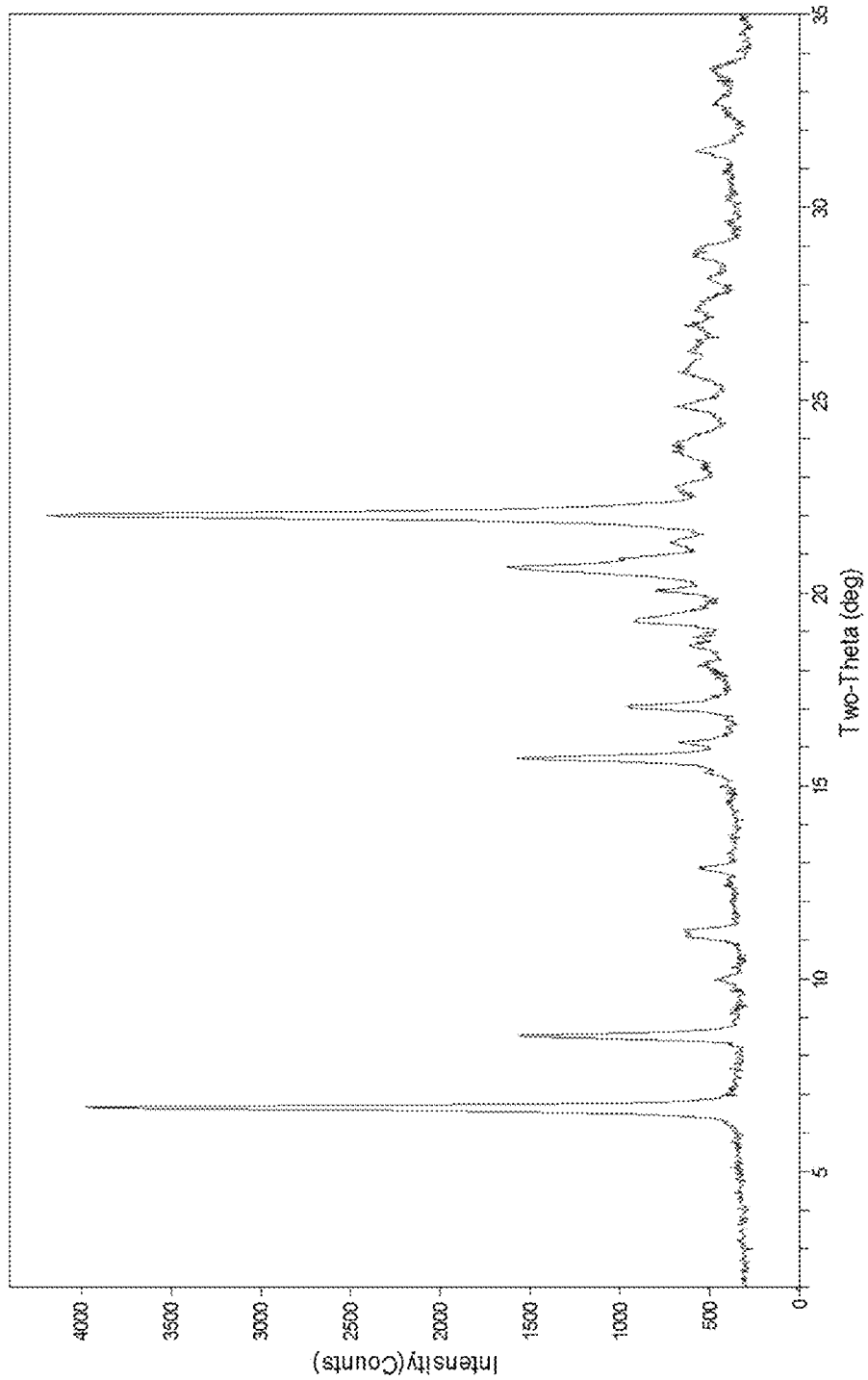
Figure 2-N:
PXRD Pattern of Monohydrochloride Salt, Crystalline Form III Oxidative Stability of S-Mandelate Salt (1:1 Stoichiometry), Anhydrate; Hydrochloride Salt, Crystalline Form II; and Atrasentan Parent, Anhydrate Intrinsic Dissolution Rate (IDR) of Atrasentan Parent, Hemi-Hydrate, and S-Mandelate Salt (1:1 Stoichiometry), Anhydrate, as a Function of pH Intrinsic Dissolution Rate (IDR) of S-Mandelate Salt (1:1 Stoichiometry), Anhydrate, and Hydrochloride Salt, Crystalline Form II, as a Function of Chloride Ion Concentration [Cl⁻]

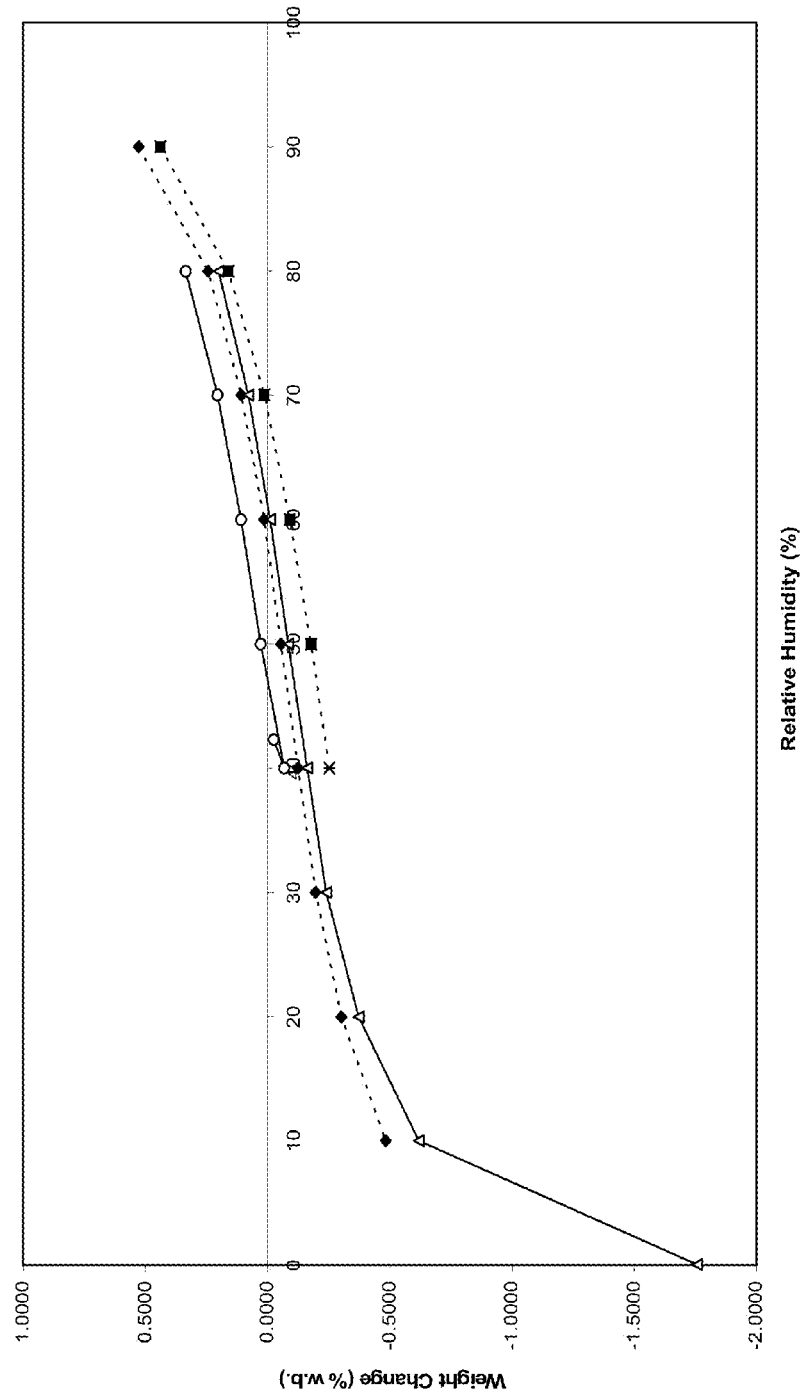
Figure 6-A: Moisture Sorption Isotherm
Hemi-Sulfate Salt (1:1 Stoichiometry), Monohydrate

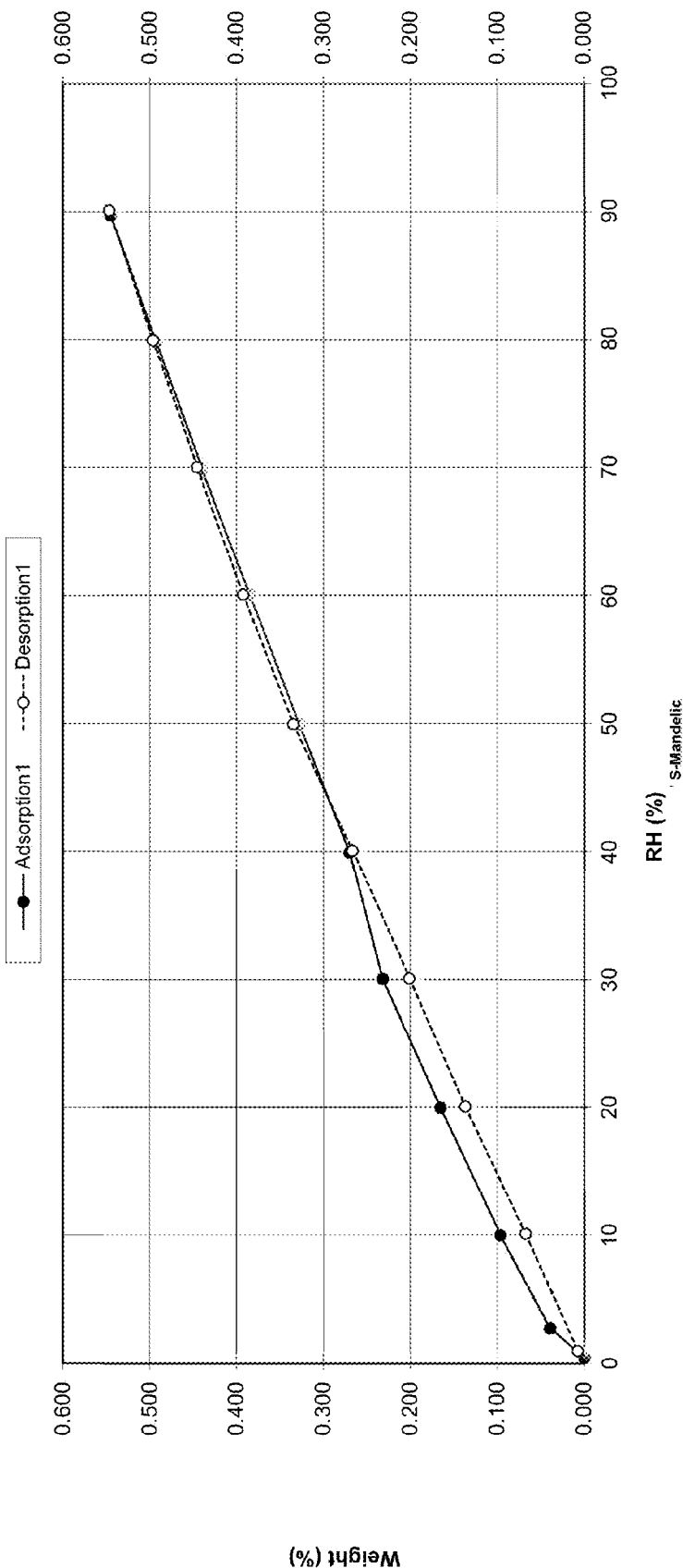

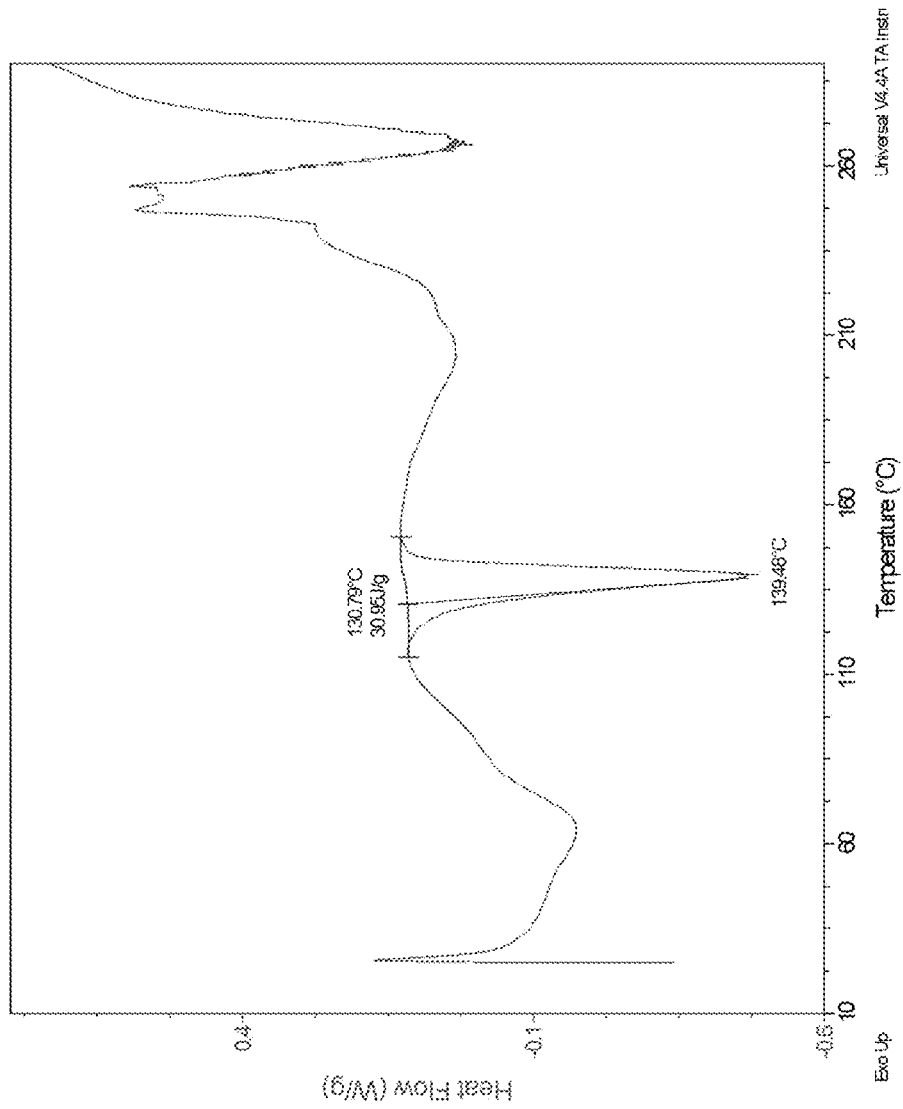

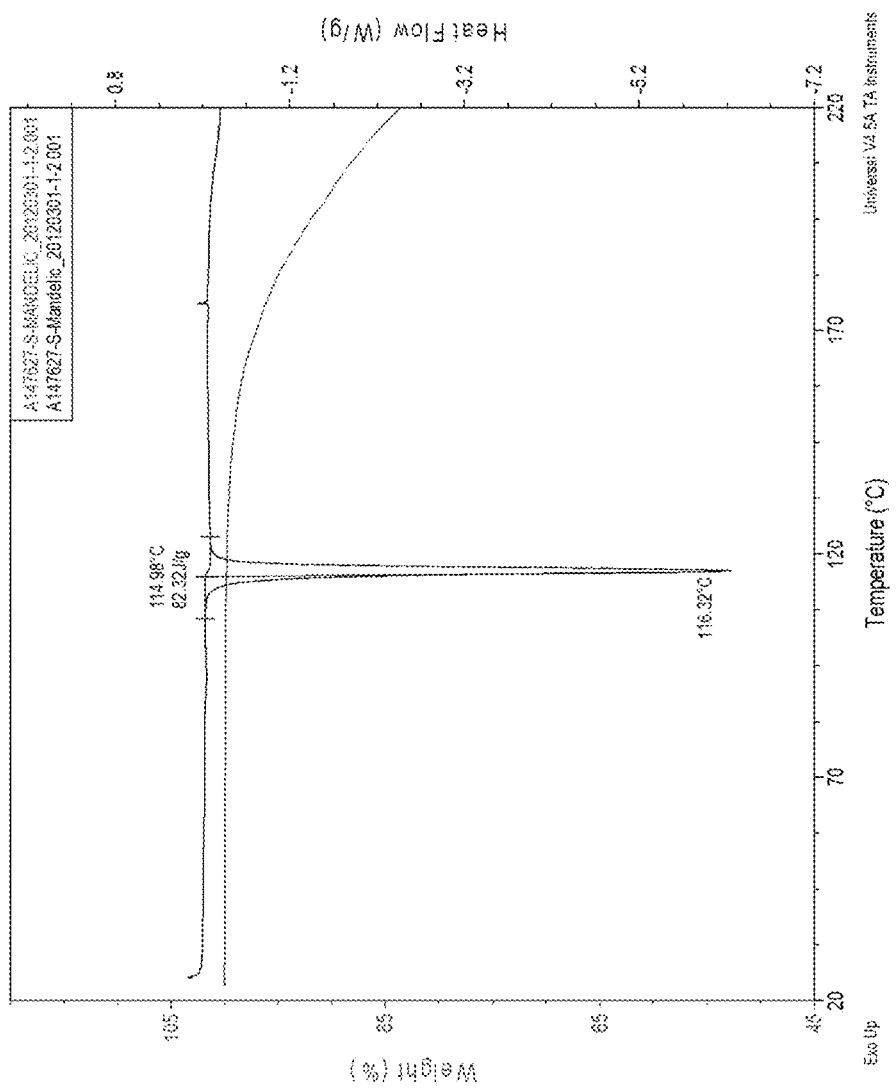
Figure 7-B: Differential Scanning Calorimetry Curve
S-Mandelate Salt (1:1 Stoichiometry), Anhydrate

ATRASENTAN MANDELATE SALTS

CROSS-REFERENCE TO RELATED APPLICATION

This application claims priority to U.S. Provisional Application Ser. No. 61/877,101 filed on Sep. 12, 2013. The entire text of that provisional application is incorporated by reference into this application.

FIELD OF THE INVENTION

The present disclosure relates to: (a) mandelate salts of atrasentan, (b) pharmaceutical compositions comprising an atrasentan mandelate salt, and, optionally, one or more additional therapeutic agents; (b) methods of using an atrasentan mandelate salt to treat nephropathy, chronic kidney disease, and/or other conditions; (c) kits comprising a first pharmaceutical composition comprising an atrasentan mandelate salt, and, optionally, a second pharmaceutical composition comprising one or more additional therapeutic agents; (d) methods for the preparation of an atrasentan mandelate salt; and (e) atrasentan mandelate salts prepared by such methods.

BACKGROUND OF THE INVENTION

Atrasentan is a potent and selective antagonist for the endothelin A ($ET_A$) receptor. It previously was evaluated in clinical trials for the treatment of prostate cancer and is now being evaluated in clinical trials for the treatment of chronic kidney disease associated with Type II diabetes.

The compound atrasentan was first reported in U.S. Pat. No. 5,767,144. Subsequently, several published international applications reported atrasentan monohydrochloride salts. WO2006/034085 reports amorphous atrasentan monohydrochloride. WO2006/034094 reports crystalline Form I of atrasentan monohydrochloride. WO2006/034084 reports crystalline Form II of atrasentan monohydrochloride. WO2006/034234 reports crystalline Form III of atrasentan monohydrochloride.

The preparation of atrasentan monohydrochloride and corresponding pharmaceutical formulations containing atrasentan monohydrochloride presents a number of manufacturing challenges that are discussed in greater detail below. There is a present need for pharmaceutically acceptable, alternative salts of atrasentan that reduce or eliminate the manufacturing challenges encountered with respect to the monohydrochloride salt.

SUMMARY OF THE INVENTION

The present disclosure relates to atrasentan mandelate salts. In one aspect, the salt is an atrasentan S-mandelate salt. In another aspect, the salt is an atrasentan R-mandelate salt.

In one aspect, the present disclosure relates to pharmaceutical compositions comprising an atrasentan mandelate salt and a pharmaceutically acceptable carrier.

In another aspect, the present disclosure relates to pharmaceutical compositions comprising an atrasentan mandelate salt, and further comprising one or more additional therapeutic agents.

In another aspect, the present disclosure relates to methods of treating nephropathy in a human subject suffering from or susceptible to nephropathy comprising administering to the subject a therapeutically effective amount of an atrasentan mandelate salt.

In another aspect, the present disclosure relates to methods of treating chronic kidney disease in a human subject suffering from or susceptible to chronic kidney disease comprising administering to the subject a therapeutically effective amount of an atrasentan mandelate salt.

In another aspect, the present disclosure relates to methods of reducing the urinary-albumin-to-creatinine ratio in a human subject suffering from or susceptible to chronic kidney disease comprising administering to the subject a therapeutically effective amount of an atrasentan mandelate salt.

In another aspect, the present disclosure relates to methods of reducing the rate of increase in serum creatinine concentration in a human subject suffering from or susceptible to chronic kidney disease, comprising administering to the subject a therapeutically effective amount of an atrasentan mandelate salt.

In another aspect, the present disclosure relates to methods of treatment comprising administering a therapeutically effective amount of an atrasentan mandelate salt, in combination with one or more additional therapeutic agents (e.g., an inhibitor of one or more elements of the renin-angiotensin-aldosterone system).

In another aspect, the present disclosure relates to kits comprising one or more pharmaceutical compositions comprising an atrasentan mandelate salt. The kit optionally can comprise one or more additional therapeutic agents and/or instructions, for example, instructions for using the kit.

In another aspect, the present disclosure relates to methods for the preparation of an atrasentan mandelate salt, wherein the method comprises the steps of (a) contacting atrasentan with a solvent comprising mandelic acid to form the atrasentan mandelate salt, and (b) isolating the atrasentan mandelate salt.

In another aspect, the present disclosure relates to atrasentan mandelate salts prepared in accordance with the method comprising the steps of (a) contacting atrasentan with a solvent comprising mandelic acid to form the atrasentan mandelate salt, and (b) isolating the atrasentan mandelate salt.

BRIEF DESCRIPTION OF THE DRAWINGS

FIG. 1-A is a microscopic image of atrasentan hemi-sulfate salt (1:1 stoichiometry), monohydrate.

FIG. 1-B is a microscopic image of for atrasentan S-mandelate salt (1:1 stoichiometry), anhydrate.

FIG. 1-C is a microscopic image of atrasentan monohydrochloride salt, crystalline Form II.

FIG. 2-A is an X-ray powder diffraction pattern for atrasentan hemi-sulfate salt (1:1 stoichiometry), monohydrate.

FIG. 2-B is an X-ray powder diffraction pattern for atrasentan S-mandelate salt (1:1 stoichiometry), anhydrate.

FIG. 2-C is an X-ray powder diffraction pattern for atrasentan S-mandelate salt (1:1 stoichiometry) crystallized from acetonitrile.

FIG. 2-D is an X-ray powder diffraction pattern for atrasentan S-mandelate salt (1:1 stoichiometry) crystallized from ethanol.

FIG. 2-E is an X-ray powder diffraction pattern for atrasentan S-mandelate salt (1:1 stoichiometry) crystallized from pyridine.

FIG. 2-F is an X-ray powder diffraction pattern for atrasentan S-mandelate salt (2:1 stoichiometry), hydrate.

FIG. 2-G is an X-ray powder diffraction pattern for atrasentan R-mandelate salt (1:1 stoichiometry), anhydrate.

FIG. 2-H is an X-ray powder diffraction pattern for atrasentan n-butylamine salt (1:1 stoichiometry), anhydrate.

FIG. 2-I is an X-ray powder diffraction pattern for atrasentan parent, anhydrate.

FIG. 2-J is an X-ray powder diffraction pattern for atrasentan parent, quarter-hydrate.

FIG. 2-K is an X-ray powder diffraction pattern for atrasentan parent, hemi-hydrate.

FIG. 2-L is an X-ray powder diffraction pattern for atrasentan monohydrochloride salt, crystalline Form I.

FIG. 2-M is an X-ray powder diffraction pattern for atrasentan monohydrochloride salt, crystalline Form II.

FIG. 2-N is an X-ray powder diffraction pattern for atrasentan monohydrochloride salt, crystalline Form III.

FIG. 6-A is a moisture sorption isotherm for atrasentan hemi-sulfate salt (1:1 stoichiometry), monohydrate.

FIG. 6-B is a moisture sorption isotherm for atrasentan S-mandelate salt (1:1 stoichiometry), anhydrate.

FIG. 7-A is a differential scanning calorimetry curve for atrasentan hemi-sulfate salt (1:1 stoichiometry), monohydrate.

FIG. 7-B is a differential scanning calorimetry curve for atrasentan S-mandelate salt (1:1 stoichiometry), anhydrate.

DETAILED DESCRIPTION OF THE INVENTION

Figure 3:
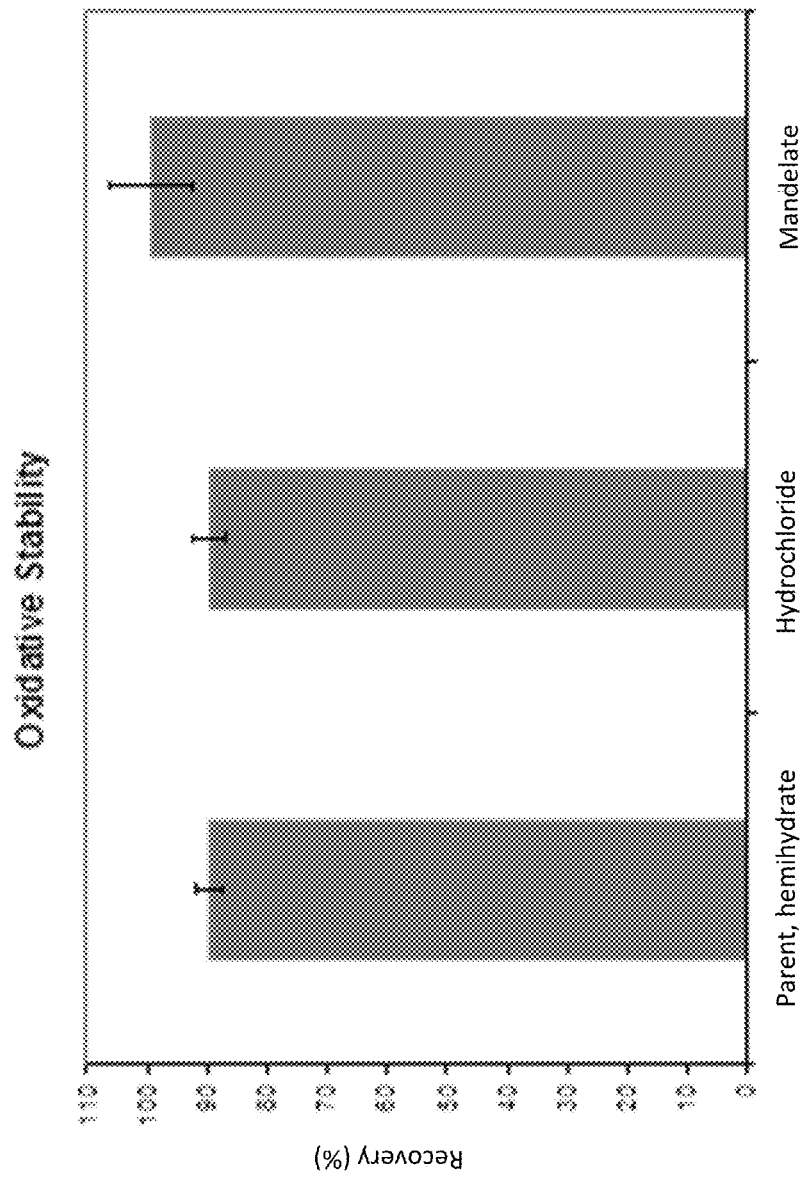
FIG. 3 is a bar chart illustrating the oxidative stability of atrasentan S-mandelate (1:1 stoichiometry), anhydrate; atrasentan monohydrochloride, crystalline Form II; and atrasentan parent, hemihydrate.

This written description uses examples to disclose the invention, including the best mode, and also to enable any person skilled in the art to practice the invention, including making and using any of the disclosed salts, substances, or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

I. Definitions

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

The term "amorphous" as applied to an atrasentan mandelate salt refers to a solid state wherein the atrasentan mandelate salt molecules are present in a disordered arrangement and do not form a distinguishable crystal lattice or unit cell. When subjected to X-ray powder diffraction, an amorphous atrasentan mandelate salt does not produce any characteristic crystalline peaks.

The term "atrasentan" refers to the compound (2R,3R,4S)-4-(1,3-benzodioxol-5-yl)-1-[2-(dibutylamino)-2-oxo ethyl]-2-(4-methoxyphenyl)pyrrolidine-3-carboxylic acid which has the structure shown below:

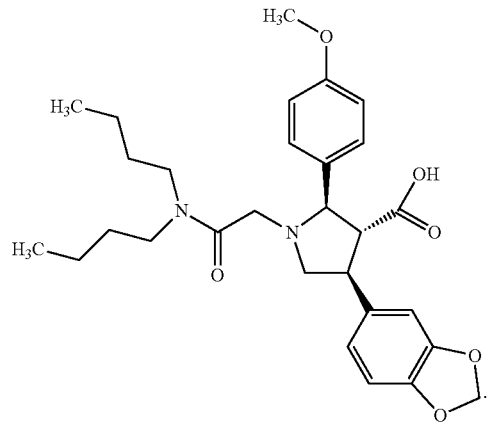 [SMILES: CCCCN(CCCC)C(=O)CN1C[C@H](c2ccc3c(c2)OCO3)[C@@H](C(=O)O)[C@@H]1c1ccc(OC)cc1]

The term "atrasentan parent" as used throughout this disclosure is intended to encompass the parent form (i.e., non-salt form) of the compound shown, including any zwitterionic form of the compound. Unless otherwise stated, any reference to an amount of atrasentan mandelate salt in this disclosure is based on the atrasentan parent equivalent weight. For example, 0.75 mg of atrasentan refers to 0.75 mg of atrasentan parent or an equivalent amount of an atrasentan mandelate salt. Methods for making atrasentan are described, for example, in U.S. Pat. Nos. 5,731,434; 5,622,971; 5,767,144; 6,162,927; 6,380,241; 6,462,194; 6,946,481; 7,208,517; and 7,365,093. The contents of these patents are incorporated by reference in this application.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "crystalline" as applied to an atrasentan mandelate salt refers to a solid state form wherein the atrasentan mandelate salt molecules are arranged to form a distinguishable crystal lattice (i) comprising distinguishable unit cells, and (ii) yielding diffraction peaks when subjected to X-ray radiation.

The term "crystalline purity" means the crystalline purity of an atrasentan mandelate salt with regard to a particular crystalline form of the atrasentan mandelate salt as determined by the powder X-ray diffraction analytical methods described in this application.

The term "crystallization" as used throughout this application can refer to crystallization and/or recrystallization depending upon the applicable circumstances relating to the preparation of the atrasentan mandelate salt.

The term "mandelic acid" refers to the compound 2-hydroxy-2-phenylacetic acid which has the structure shown below:

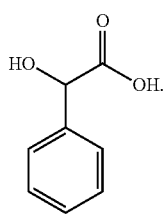

The stereoisomers of mandelic acid are characterized as "R" or "S" depending on the configuration of substituents around the chiral carbon atom. The terms "R" and "S" are configurations as defined in IUPAC 1974 Recommendations for Section E, Fundamental Stereochemistry, Pure Appl. Chem., 1976, 45: 13-30.

The term "pharmaceutically acceptable" (such as in the recitation of a "pharmaceutically acceptable salt" or a "pharmaceutically acceptable diluent") refers to a material that is compatible with administration to a subject, e.g., the material does not cause an undesirable biological effect. Examples of pharmaceutically acceptable salts are described in "Handbook of Pharmaceutical Salts: Properties, Selection, and Use" by Stahl and Wermuth (Wiley-VCH, Weinheim, Germany, 2002). Examples of pharmaceutically acceptable excipients are described in the "Handbook of Pharmaceutical Excipients," Rowe et al., Ed. (Pharmaceutical Press, 7th Ed., 2012).

The term "subject" refers to an animal. In one aspect, the animal is a mammal, including a human or non-human, preferably a human subject.

The terms "treating" and "treatment" refer to ameliorating, suppressing, eradicating, reducing the severity of, decreasing the frequency of incidence of, preventing, reducing the risk of, or delaying the onset of the condition.

The abbreviation "PXRD" means powder X-ray diffraction.

The abbreviation "UACR" refers to urinary-albumin-to-creatinine ratio.

The abbreviation "v/v" refers to volume/volume.

II. Atrasentan Mandelate Salts

The present disclosure relates to atrasentan mandelate salts. As with all pharmaceutical compounds and compositions, the chemical and physical properties of atrasentan are important in its commercial development. These properties include, but are not limited to: (1) packing properties such as molar volume, bulk density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, the processing and storage of atrasentan and pharmaceutical compositions comprising atrasentan. Salts, particularly crystalline salts, of atrasentan that improve upon one or more of these properties relative to other salts and/or solid state forms of atrasentan are desirable.

The atrasentan dosage forms prepared and administered in clinical trials to date have contained crystalline Form II atrasentan monohydrochloride (reported in WO2006/034084). Form II is the most thermodynamically stable of the three crystalline forms of atrasentan monohydrochloride salts that have been identified (i.e., Form I, Form II, and Form III).

Although atrasentan clinical trials have proceeded with crystalline Form II of atrasentan monohydrochloride, efforts have continued to identify alternative atrasentan salts that provide further advantages relative to the monohydrochloride salt.

For example, one property of the crystalline Form I, Form II, and Form III atrasentan monohydrochloride salts that could be beneficially improved is crystal morphology. All of the known atrasentan monohydrochloride salts have a needle morphology that can create challenges during the preparation and formulation of such salts. For example, the needle morphology results in a relatively low bulk powder density that makes powder handling more difficult during the preparation of the atrasentan dosage form. The needle morphology also increases the difficulty of filtration, requiring a longer time in solid-liquid separation. These problems reduce the efficiency of the atrasentan purification (since the mother liquor will be enriched in impurities), increase energy consumption (due to removal of excess residual organic solvent in compliance with International Conference on Harmonization guidelines), and potentially lead to sintering or caking of the solid that may require an additional milling step.

Another property of the monohydrochloride salt that could be beneficially improved is corrosivity. The preparation of the crystalline Form I, Form II, and Form III atrasentan monohydrochloride salts requires the use and handling of corrosive hydrochloric acid and typically is carried out in a glass-lined reactor rather than a standard stainless steel reactor. In addition, during the preparation of the atrasentan monohydrochloride dosage form, the monohydrochloride salt can cause corrosion of the tooling (such as the punch and die of the tablet press) over time. Further, the monohydrochloride salt potentially can decompose to yield hydrogen chloride gas over time and/or at higher temperatures.

Prior efforts to prepare suitable crystalline forms of atrasentan (including crystalline atrasentan parent, crystalline atrasentan salts other than hydrochloride salts, co-crystals, and crystalline ionic or molecular adducts) have been unsuccessful. Applicant, however, has now succeeded in preparing and isolating crystalline atrasentan mandelate salts and has discovered that such salts have several advantages over the monohydrochloride salt. The mandelate salts exhibit improved crystal morphology and either have a reduced aspect ratio (the ratio of the height of a particle to the cross-sectional dimension of a particle) and are less needle-like or have a plate or prismatic shape. This crystal morphology results in a higher bulk powder density and improved powder handling properties for the mandelate salt. For example, a 120 mg tablet containing 0.75 mg of atrasentan will have a drug loading of 0.67% for the hydrochloride salt (i.e., 0.8025 mg of the hydrochloride salt per tablet) compared to a drug loading of 0.88% for the mandelate salt (i.e., 1.05 mg of the mandelate salt per tablet). As the drug loading increases, the likelihood of achieving acceptable content uniformity also increases. In addition, the improvement in crystal morphology also facilitates solid-liquid separation during filtration.

The mandelate salts also represent an improvement over the hydrochloride salts with respect to corrosivity. There is no need to handle corrosive hydrochloric acid during the preparation of the mandelate salt. Further, the previously-discussed concerns regarding corrosion of tooling and longer-term chemical stability associated with the monohydrochloride salt are materially reduced for the mandelate salt.

Accordingly, in one embodiment the disclosure relates to an atrasentan mandelate salt. In one aspect, the salt is an atrasentan S-mandelate salt. In another aspect, the salt is an atrasentan R-mandelate salt. The atrasentan mandelate salt can be in the form of an anhydrate, a hydrate, or a solvate.

In another embodiment, the salt is a crystalline atrasentan S-mandelate salt. In another aspect, the atrasentan S-mandelate salt is an amorphous salt. In another aspect, the atrasentan S-mandelate salt is an anhydrous salt. In another aspect, the atrasentan S-mandelate salt is a solvated salt. In another aspect, the atrasentan S-mandelate salt is a solvated salt selected from the group consisting of an acetonitrile solvate, an ethanol solvate, and a pyridine solvate. In another aspect, the atrasentan S-mandelate salt is a hydrated salt.

In another embodiment, the salt is a crystalline atrasentan R-mandelate salt. In another aspect, the atrasentan R-mandelate salt is an amorphous salt. In another aspect, the atrasentan R-mandelate salt is an anhydrous salt. In another aspect, the atrasentan R-mandelate salt is a solvated salt. In another aspect, the atrasentan R-mandelate salt is a hydrated salt.

(a) S-Mandelate Salt (1:1 Stoichiometry)

In one embodiment, the salt is a crystalline atrasentan S-mandelate salt wherein the molar ratio of atrasentan to S-mandelate is about 1:1. In one aspect, the atrasentan S-mandelate salt is an anhydrous salt. In another aspect, the atrasentan S-mandelate salt is a solvated salt. In another aspect, the atrasentan S-mandelate salt is a solvated salt selected from the group consisting of an acetonitrile solvate, an ethanol solvate, and a pyridine solvate. In another aspect, the atrasentan S-mandelate salt is a hydrated salt.

In another embodiment, the salt is a crystalline S-mandelate salt having an X-ray powder diffraction pattern comprising peaks at 5.5±0.2, 9.7±0.2, and 19.4±0.2 degrees two theta when measured at about 25° C. with monochromatic Kα1 radiation. In one aspect, the salt is a crystalline S-mandelate salt having an X-ray powder diffraction pattern comprising peaks at 5.5±0.2, 9.7±0.2, 12.1±0.2, and 19.4±0.2 degrees two theta when measured at about 25° C. with monochromatic Kα1 radiation. In another aspect, the salt is a crystalline S-mandelate salt having an X-ray powder diffraction pattern comprising peaks at 5.5±0.2, 9.7±0.2, 12.1±0.2, 18.0±0.2, 18.4±0.2, and 19.4±0.2 degrees two theta when measured at about 25° C. with monochromatic Kα1 radiation. In another aspect, the experimental error associated with the X-ray powder diffraction peak values recited in the various embodiments above is ±0.1 degrees two theta. In another aspect, the salt is an anhydrous salt. In another aspect, the molar ratio of atrasentan to S-mandelate is about 1:1.

In another embodiment, the salt is a crystalline S-mandelate salt having an orthorhombic lattice type. In one aspect, the salt has a P212121 space group. In another aspect, the salt has unit cell a, b and c values of about 9.954 Å, about 11.049 Å, and about 30.861 Å, respectively. In another aspect, the salt has unit cell α, β and γ values of about 90°, about 90°, and about 90°, respectively. In another aspect, the salt has at least three or more of the following properties: (a) an orthorhombic lattice type, (b) a P212121 space group, (c) unit cell a, b and c values of about 9.954 Å, about 11.049 Å, and about 30.861 Å, respectively, and/or (d) unit cell α, β and γ values of about 90°, about 90°, and about 90°, respectively. In another aspect, the salt has: (a) an orthorhombic lattice type, (b) a P212121 space group, (c) unit cell a, b and c values of about 9.954 Å, about 11.049 Å, and about 30.861 Å, respectively, and (d) unit cell α, β and γ values of about 90°, about 90°, and about 90°, respectively. In another aspect, the salt is an anhydrous salt. In another aspect, the molar ratio of atrasentan to S-mandelate is about 1:1.

(b) S-Mandelate Salt (2:1 Stoichiometry)

In one embodiment, the salt is a crystalline atrasentan S-mandelate salt wherein the molar ratio of atrasentan to S-mandelate is about 2:1. In one aspect, the atrasentan S-mandelate salt is an anhydrous salt. In another aspect, the atrasentan S-mandelate salt is a solvated salt. In another aspect, the atrasentan S-mandelate salt is a hydrated salt.

In another embodiment, the salt is a crystalline S-mandelate salt having an X-ray powder diffraction pattern comprising peaks at 4.5±0.2, 8.6±0.2, and 18.1±0.2 degrees two theta when measured at about 25° C. with monochromatic Kα1 radiation. In one aspect, the salt is a crystalline S-mandelate salt having an X-ray powder diffraction pattern comprising peaks at 4.5±0.2, 8.6±0.2, 18.1±0.2, and 18.7±0.2 degrees two theta when measured at about 25° C. with monochromatic Kα1 radiation. In another aspect, the salt is a crystalline S-mandelate salt having an X-ray powder diffraction pattern comprising peaks at 4.5±0.2, 8.6±0.2, 9.1±0.2, 18.1±0.2, and 18.7±0.2 degrees two theta when measured at about 25° C. with monochromatic Kα1 radiation. In another aspect, the experimental error associated with the X-ray powder diffraction peak values recited in the various embodiments above is ±0.1 degrees two theta. In another aspect, the salt is an anhydrous salt. In another aspect, the salt is a hydrated salt.

(c) R-Mandelate Salt (1:1 Stoichiometry)

In one embodiment, the salt is a crystalline atrasentan R-mandelate salt wherein the molar ratio of atrasentan to R-mandelate is about 1:1. In one aspect, the atrasentan R-mandelate salt is an anhydrous salt. In another aspect, the atrasentan R-mandelate salt is a solvated salt. In another aspect, the atrasentan R-mandelate salt is a hydrated salt.

In another embodiment, the salt is a crystalline R-mandelate salt having an X-ray powder diffraction pattern comprising peaks at 5.7±0.2, 11.8±0.2, and 20.9±0.2 degrees two theta when measured at about 25° C. with monochromatic Kα1 radiation. In one aspect, the salt is a crystalline R-mandelate salt having an X-ray powder diffraction pattern comprising peaks at 5.7±0.2, 8.2±0.2, 11.8±0.2, and 20.9±0.2 degrees two theta when measured at about 25° C. with monochromatic Kα1 radiation. In another aspect, the salt is a crystalline R-mandelate salt having an X-ray powder diffraction pattern comprising peaks at 5.7±0.2, 8.2±0.2, 8.6±0.2, 11.8±0.2, and 20.9±0.2 degrees two theta when measured at about 25° C. with monochromatic Kα1 radiation. In another aspect, the experimental error associated with the X-ray powder diffraction peak values recited in the various embodiments above is ±0.1 degrees two theta. In another aspect, the salt is an anhydrous salt.

III. Methods of Treatment

The present disclosure also relates to methods of treating a condition in a subject, particularly a human subject suffering from or susceptible to the condition, comprising administering to the subject a therapeutically effective amount of an atrasentan mandelate salt as described in the present disclosure.

In one embodiment, the present disclosure relates to methods of treating nephropathy in a human subject suffering from or susceptible to nephropathy comprising administering to the subject a therapeutically effective amount of an atrasentan mandelate salt. In a further aspect, the nephropathy treated is diabetic nephropathy. In a further aspect, the subject selected for treatment is suffering from diabetic nephropathy. In a further aspect, the subject selected for treatment is suffering from type 2 diabetes mellitus. In a further aspect, the subject selected for treatment is suffering from one or more of the following conditions: (a) diabetic nephropathy; (b) type 2 diabetes; (c) Stage 3 chronic kidney disease, Stage 4 chronic kidney disease, or end stage renal disease; (d) a urinaryalbumin-to-creatinine ratio greater than about 30 mg/g (i.e., the subject is suffering from microalbuminuria); (e) a urinary-albumin-to-creatinine ratio greater than about 300 mg/g (i.e., the subject is suffering from macroalbuminuria); and/or (f) an estimated glomerular filtration rate from about 25 ml/min/ 173 m$^2$ to about 59 ml/min/173 m$^2$. In a further aspect, the subject is also administered a second therapeutic agent that inhibits one or more elements of the renin-angiotensin-aldosterone system. In a further aspect, the second therapeutic agent that inhibits one or more elements of the renin-angiotensin-aldosterone system is selected from the group consisting of diuretics, angiotensin converting enzyme inhibitors, angiotensin II receptor blockers, calcium channel blockers, renin inhibitors, and aldosterone antagonists. In a further aspect, the second therapeutic agent that inhibits one or more elements of the renin-angiotensin-aldosterone system is selected from the group consisting of angiotensin converting enzyme inhibitors and angiotensin II receptor blockers.

In another embodiment, the present disclosure relates to methods of treating chronic kidney disease in a human subject suffering from or susceptible to chronic kidney disease comprising administering to the subject a therapeutically effective amount of an atrasentan mandelate salt. In a further aspect, the chronic kidney disease is Stage 3 or Stage 4 chronic kidney disease. In a further aspect, the chronic kidney disease is end stage renal disease. In a further aspect, the treatment delays progression of chronic kidney disease in the subject. In a further aspect, the treatment delays progression of end stage renal disease in the subject. In a further aspect, the subject selected for treatment is suffering from diabetic nephropathy. In a further aspect, the subject selected for treatment is suffering from type 2 diabetes mellitus. In a further aspect, the subject selected for treatment is suffering from Stage 3 or Stage 4 chronic kidney disease. In a further aspect, the subject selected for treatment is suffering from end stage renal disease. In a further aspect, the subject selected for treatment is suffering from one or more of the following conditions: (a) diabetic nephropathy; (b) type 2 diabetes; (c) Stage 3 chronic kidney disease, Stage 4 chronic kidney disease, or end stage renal disease; (d) a urinary-albumin-to-creatinine ratio greater than about 30 mg/g; (e) a urinary-albumin-to-creatinine ratio greater than about 300 mg/g; and/or (f) an estimated glomerular filtration rate from about 25 ml/min/1.73 m$^2$ to about 59 ml/min/173 m$^2$. In a further aspect, the subject is also administered a second therapeutic agent that inhibits one or more elements of the renin-angiotensin-aldosterone system. In a further aspect, the second therapeutic agent that inhibits one or more elements of the renin-angiotensin-aldosterone system is selected from the group consisting of diuretics, angiotensin converting enzyme inhibitors, angiotensin II receptor blockers, calcium channel blockers, renin inhibitors, and aldosterone antagonists. In a further aspect, the second therapeutic agent that inhibits one or more elements of the renin-angiotensin-aldosterone system is selected from the group consisting of angiotensin converting enzyme inhibitors and angiotensin II receptor blockers.

In another embodiment, the present disclosure relates to methods of reducing the urinary-albumin-to-creatinine ratio in a human subject suffering from or susceptible to chronic kidney disease comprising administering to the subject a therapeutically effective amount of an atrasentan mandelate salt.

In another embodiment, the present disclosure relates to methods of reducing the rate of increase in serum creatinine concentration in a human subject suffering from or susceptible to chronic kidney disease comprising administering to the subject a therapeutically effective amount of an atrasentan mandelate salt.

In additional embodiments, the amount of the atrasentan mandelate salt administered to the subject in any of the above-described methods is from about 0.25 mg daily to about 1.25 mg daily on an atrasentan parent equivalent weight basis. In one aspect, the amount of the atrasentan mandelate salt administered to the subject is from about 0.40 mg daily to about 1.00 mg daily on an atrasentan parent equivalent weight basis. In another aspect, the amount of the atrasentan mandelate salt administered to the subject is from about 0.40 mg daily to about 0.85 mg daily on an atrasentan parent equivalent weight basis. In another aspect, the amount of the atrasentan mandelate salt administered to the subject is about 0.50 mg daily on an atrasentan parent equivalent weight basis. In another aspect, the amount of the atrasentan mandelate salt administered to the subject is about 0.75 mg daily on an atrasentan parent equivalent weight basis.

In another embodiment, the present disclosure relates to the use of an atrasentan mandelate salt for treating a condition as described in the various embodiments of the disclosure.

In another embodiment, the present disclosure relates to the use of an atrasentan mandelate salt in the preparation of a medicament for treating a condition as described in the various embodiments of the disclosure.

IV. Pharmaceutical Compositions

The present disclosure also relates to pharmaceutical compositions comprising an atrasentan mandelate salt as described in the present disclosure, and a pharmaceutically acceptable carrier. Such pharmaceutical compositions can be formulated for various routes of systemic or local delivery for example, by oral administration, topical administration, transmucosal administration, rectal administration, intravaginal administration, or administration by subcutaneous, intrathecal, intravenous, intramuscular, intraperitoneal, intranasal, intraocular or intraventricular injection.

The pharmaceutical compositions often further comprise one or more pharmaceutically acceptable excipients in addition to the carrier. The term "excipient" is used in this application to describe any ingredient other than atrasentan, or a pharmaceutically acceptable salt thereof, or another pharmacological agent. The choice of excipient(s) will depend to a large extent on factors such as the particular mode of administration, the effect of the excipient on solubility and stability, and the nature of the dosage form. The pharmaceutical compositions can be formulated for immediate release or modified release. Modified release formulations include delayed-, sustained-, pulsed-, controlled-, targeted and programmed release formulations. Methods generally known in the art can be employed to manufacture the pharmaceutical compositions of the present invention, e.g., conventional granulating, mixing, dissolving, encapsulating, lyophilizing, emulsifying, or levigating processes, among others. The pharmaceutical compositions discussed below are given by way of example and should not be construed as limiting the present invention.

(d) Oral Administration

For oral, buccal, and sublingual administration, the atrasentan mandelate salt can be formulated as a solid dosage form such as a powder, suspension, granule, tablet, pill, capsule, gelcap, or caplet. These solid dosage forms can be prepared, for example, by mixing the atrasentan mandelate salt with at least one excipient such as sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethylcellulose, and/or polyvinylpyrrolidone. Solid dosage forms optionally can contain additional excipients to aid in administration, such as an inactive diluent, a lubricant (such as magnesium stearate), a preservative (such as a paraben acid or sorbic acid), an antioxidant (such as ascorbic acid, tocopherol or cysteine), a disintegrating agent, a binder, a thickener, a buffer, a sweetener, a flavoring agent, or a perfuming agent. Dyestuffs or pigments can be added to the pharmaceutical composition for identification. Tablets and pills can be further treated with suitable coating materials known in the art (e.g., enteric coating materials).

Atrasentan mandelate salts also can be formulated for oral administration as a liquid dosage form such as an emulsion, syrup, elixir, suspension, slurry, or solution. Such liquid dosage forms generally contain one or more pharmaceutically acceptable excipients in addition to the atrasentan mandelate salt, e.g., a sterile liquid (such as water, an oil, an alcohol, or a combination of these excipients), a surfactant, a suspending agent, or an emulsifying agent. Examples of pharmaceutically acceptable oils include peanut oil, sesame oil, cottonseed oil, corn oil, olive oil and mixtures of oils. Examples of pharmaceutically acceptable alcohols include ethanol, isopropyl alcohol, hexadecyl alcohol, glycerol and propylene glycol. Additionally, liquid suspensions can also contain, for example, esters of fatty acids (such as ethyl oleate, isopropyl myristate, fatty acid glycerides and acetylated fatty acid glycerides) and ethers (such as poly(ethyleneglycol)), petroleum hydrocarbons including mineral oil and petrolatum.

(e) Parenteral Administration

The atrasentan mandelate salt can be formulated for administration by injection, e.g., by subcutaneous, intrathecal, intravenous, intramuscular, intraperitoneal, intranasal, intraocular or intraventricular injection. Such injectable dosage forms can be in solution phase or in the form of a suspension (such as an aqueous suspension or oil suspension employing a suitable dispersant or wetting agent and a suspending agent). Injectable dosage forms generally are prepared using a solvent or diluent. Pharmaceutically acceptable solvents or vehicles include sterilized water, Ringer's solution, and isotonic aqueous saline solution. Alternatively, sterile oils or fatty acids can be employed as solvents or suspending agents. Generally, the oil or fatty acid is non-volatile, including natural or synthetic oils, fatty acids, mono-, di- or tri-glycerides.

Injectable dosage forms also can be prepared as a powder suitable for reconstitution with an appropriate vehicle as described above. Examples of these injectable dosage forms include freeze-dried powders, rotary-dried powders, spray-dried powders, amorphous powders, granules, precipitates, and particulates.

Injectable dosage forms optionally can contain additional excipients including stabilizers, cyclodextrins (such as a beta-cyclodextrin), pH modifiers, surfactants, bioavailability modifiers, and combinations of these excipients. They can be formulated for administration by bolus injection or continuous infusion. A unit dosage form for injection can be in ampoules or in multi-dose containers.

(f) Topical Administration

The atrasentan mandelate salt can be formulated for administration topically to the skin or mucosa, i.e., dermally or transdermally. Topical formulations include, e.g., gels, hydrogels, lotions, solutions, creams, ointments, dusting powders, dressings, foams, films, skin patches, wafers, implants, sponges, fibers, bandages and microemulsions. Typical carriers used in topical formulations include, e.g., alcohol, water, mineral oil, liquid petrolatum, white petrolatum, glycerin, polyethylene glycol and propylene glycol. Topical formulations may also employ liposomes and penetration enhancers.

(g) Inhaled/Intranasal Administration

The atrasentan mandelate salt can be formulated for inhalation or administration nasally. These pharmaceutical formulations can be a spray or aerosol containing an appropriate solvent and optionally other excipients including stabilizers, antimicrobial agents, antioxidants, pH modifiers, surfactants, bioavailability modifiers, and combinations of these. A propellant for an aerosol formulation can include, e.g., compressed air, nitrogen, carbon dioxide, or a hydrocarbon-based, low-boiling solvent. The atrasentan mandelate salt can be conveniently delivered in the form of an aerosol spray presentation from a nebulizer or the like.

(h) Rectal/Intravaginal Administration

The atrasentan mandelate salt can be formulated for rectal or intravaginal administration. These formulations can be in the form of a suppository, pessary, ointment, enema, a tablet, or a cream for release of the atrasentan mandelate salt, such as in the intestines, sigmoid flexure and/or rectum. Rectal suppositories are prepared by mixing an atrasentan mandelate salt of the present invention with an acceptable vehicle (e.g., cocoa butter or polyethylene glycol) which is present in a solid phase at normal storing temperatures, and present in a liquid phase at those temperatures suitable to release a drug inside the body, such as in the rectum. Oils can also be employed in the preparation of formulations of the soft gelatin type and suppositories. Water, saline, aqueous dextrose and related sugar solutions, and glycerols can be employed in the preparation of suspension formulations which can also contain suspending agents such as pectins, carbomers, methyl cellulose, hydroxypropyl cellulose or carboxymethyl cellulose, as well as buffers and preservatives.

(i) Ocular and Aural Administration

The atrasentan mandelate salt can be formulated for administration directly to the eye or ear, typically in the form of drops of a micronized suspension or solution in isotonic, pH-adjusted, sterile saline. Other formulations suitable for ocular and aural administration include, e.g., ointments, biodegradable (e.g., absorbable gel sponges, collagen) and non-biodegradable (e.g., silicone) implants, wafers, lenses, and particulate or vesicular systems, such as niosomes or liposomes. Ocular and aural formulation may also incorporate additional excipients such as preservatives (such as benzalkonium chloride) and a polymer such as a crossed-linked polyacrylic acid, polyvinyl alcohol, or hyaluronic acid; a cellulosic polymer (such as hydroxypropylmethylcellulose, hydroxyethylcellulose, or methyl cellulose); or a heteropolysaccharide polymer (such as gelan gum). These formulations also may be delivered by iontophoresis.

(j) Other Technologies

The atrasentan mandelate salt may be combined with soluble macromolecular entities, such as cyclodextrin and suitable derivatives thereof or polyethylene glycol-containing polymers, in order to improve solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Alpha-, beta- and gamma-cyclodextrins are commonly used for these purposes, examples of which may be found in International Patent Applications Nos. WO1991/11172, WO1994/02518 and WO1998/55148.

The pharmaceutical compositions for administering the atrasentan mandelate salt can also comprise, for example, micelles or liposomes, or some other encapsulated form, or can be administered in an extended release form to provide a prolonged storage and/or delivery effect. Therefore, the pharmaceutical compositions can be compressed into pellets or cylinders and implanted intramuscularly or subcutaneously as depot injections or as implants such as stents. Such implants can employ known materials such as silicones and biodegradable polymers.

Besides those representative dosage forms described above, pharmaceutically acceptable excipients and carriers are generally known to those skilled in the art and are thus included in the instant invention. Such excipients and carriers are described, for example, in "Remington's Pharmaceutical Sciences," Mack Pub. Co., New Jersey (1991).

In one embodiment, the pharmaceutical composition is a solid pharmaceutical dosage form comprising from about 0.25 mg to about 1.25 mg of the atrasentan mandelate salt on an atrasentan parent equivalent weight basis. In one aspect, the pharmaceutical composition comprises from about 0.40 mg to about 1.00 mg of the atrasentan mandelate salt on an atrasentan parent equivalent weight basis. In another aspect, the pharmaceutical composition comprises from about 0.40 mg to about 0.85 mg of the atrasentan mandelate salt on an atrasentan parent equivalent weight basis. In another aspect, the pharmaceutical composition comprises from about 0.50 of the atrasentan mandelate salt on an atrasentan parent equivalent weight basis. In another aspect, the pharmaceutical composition comprises from about 0.75 of the atrasentan mandelate salt on an atrasentan parent equivalent weight basis.

In another embodiment, the pharmaceutical composition is a tablet. In one aspect, the tablet has a weight from about 37.5 mg to about 1500 mg. In another aspect, the tablet has a weight from about 50 mg to about 750 mg. In another aspect, the tablet has a weight from about 50 mg to about 250 mg. In another aspect, the tablet has a weight from about 75 mg to about 500 mg. In another aspect, the tablet has a weight from about 75 mg to about 150 mg. In another aspect, the tablet has a weight from about 100 mg to about 250 mg. In another aspect, the tablet has a weight from about 100 mg to about 230 mg.

In general, the tablet optionally can be surrounded or coated with at least one non-rate-controlling layer. The non-rate-controlling layer can be formed as a single layer, coating or membrane or a plurality of single layers, coatings or membranes. The functions of the non-rate-controlling layer can include, for example, providing further stability for the atrasentan, serving as a process aid and/or as a cosmetic enhancement for the formulation, and/or acting as a masking agent to reduce any undesired odor associated with the formulation (such as the odor commonly associated with L-cysteine).

When the dosage form comprises a non-rate-controlling layer, the non-rate-controlling layer can be made of one or more polymers, as well as, other ingredients known in the art, such as, but not limited to, plasticizers, pigments/opacifiers, waxes, etc. Examples of polymers that can be used include, but are not limited to, hydroxypropylmethylcellulose, hydroxypropyl cellulose, methylcellulose, polyvinyl alcohol and polyethylene glycol. Examples of plasticizers that can be used include, but are not limited to, polyethylene glycol(s), glycerin, triacetin, triethyl citrate, diethyl phthalate, L-cysteine, and mineral oils. Examples of pigments/opacifiers that can be used include, but are not limited to, water soluble dyes (for example, sunset yellow, quinoline yellow, erythrosine, and tartrazine), pigments (for example, aluminum lakes, titanium oxides, iron oxides and talc), and natural products (for example, riboflavin, carotenoids, chlorophyll, anthocyanins, and carmine). An example of a wax that can be used includes, but is not limited to, a paraffin wax.

In another embodiment, the dosage form is a tablet coated with a pharmaceutically acceptable polymer.

In another embodiment, the dosage form is a capsule.

In another embodiment, the dosage form is packaged in a semi-permeable container. In one aspect, the semi-permeable container is a blister pack.

In another embodiment, the dosage form is packaged in a substantially impermeable container.

In another embodiment, the dosage form is an immediate release dosage form. In one aspect, the dosage form is an immediate release tablet and releases at least about 85% of the atrasentan, or pharmaceutically acceptable salt thereof, within about 45 minutes as determined in an in vitro dissolution test conducted using a USP Dissolution Apparatus 2 (Paddle Apparatus), a 0.01N hydrochloric acid dissolution medium, and a paddle rotation of 50 RPM. In another aspect, the dosage form is an immediate release tablet and releases at least about 75% of the atrasentan mandelate salt within about 30 minutes.

V. Combination Therapy and Fixed-Dose Combinations

The methods of the present disclosure also contemplate treatments comprising administering an atrasentan mandelate salt in combination with one or more additional therapeutic agents (such as an inhibitor of one or more elements of the renin-angiotensin-aldosterone system as previously discussed above). Accordingly, the atrasentan mandelate salts of the present disclosure can be administered alone or in combination with one or more additional therapeutic agents. When administered to a subject in combination with one or more additional therapeutic agents, the atrasentan mandelate salt and additional therapeutic agent(s) can be administered as separate dosage forms or as a single dosage form comprising the atrasentan mandelate salt and the additional therapeutic agent(s) (i.e., a fixed-dose combination). If administered as a separate dosage form, the additional therapeutic agent may be administered either simultaneously with, or sequentially with, the dosage form comprising the atrasentan mandelate salt.

Representative additional therapeutic agents include, for example, diuretics, antihypertensive agents, therapeutic agents for diabetes or diabetic complications, and therapeutic agents for hyperlipidemia.

In one embodiment, the atrasentan mandelate salt may be co-administered with one or more diuretics such as hydrochlorothiazide (such as MICROZIDE™ or ORETIC™), hydroflumethiazide (such as SALURON™), bemetanide (such as BUMEX™), torsemide (such as DEMADEX™), metolazone (such as ZAROXOLYN™), chlorothiazide (such as DIURIL™, ESIDRIX™ or HYDRODIURIL™), triamterene (such as DYRENIUM™), ethacrynic acid (such as EDECRIN™), chlorthalidone (such as HYGROTON™), furosemide (such as LASIX™), indapamide (such as LOZOL™), or amiloride (such as MIDAMOR™ or MODURETIC™).

In another embodiment, the atrasentan mandelate salt may be co-administered with one or more angiotensin converting enzyme (ACE) inhibitors such as quinapril (such as ACCUPRIL™), perindopril (such as ACEON™), captopril (such as CAPOTEN™), enalapril (such as VASOTEC™), ENALAPRILAT™, ramipril (such as ALTACE™), cilazapril, delapril, fosenopril (such as MONOPRIL™) zofenopril, indolapril, benazepril (such as LOTENSIN™), lisinopril (such as PRINIVIL™ or ZESTRIL™), spirapril, trandolapril (such as MAVIK™), perindep, pentopril, moexipril (such as UNIVASC™), or pivopril.

In another embodiment, the atrasentan mandelate salt may be co-administered with one or more angiotensin II receptor blockers such as candesartan (such as ATACAND™), eprosartan (such as TEVETEN™), irbesartan (such as AVEPRO™), losartan (such as COZAAR™), olmesartan, olmesartan medoxomil (such as BENICAR™), tasosartan, telmisartan (such as MICARDIS™) valsartan (such as DIOVAN™), zolasartan, Fl-6828K, RNH-6270, UR-7198, Way-126227, KRH-594, TAK-536, BRA-657, or TA-606.

In another embodiment, the atrasentan mandelate salt may be co-administered with one or more calcium channel blockers such as nifedipine (such as ADALAT™, ADALAT CC™, or PROCARDIA™), verapamil (such as GALAN™, COVERA-HS™, ISOPTIN SR™, or VERELAN™), diltiazem (such as CARDIZEM™, CARDIZEM CD™, CARDIZEM LA™, CARDIZEM SR™ DILACOR™, TIAMATE™, or TIAZAC™), isradipine (such as DYNACIRC™ or DYNACIRC CR™), amlodipine (such as NORVASC™), felodipine (such as PLENDIL™), nisoldipine (such as SULAR™), bepridil (such as VASCOR™) vatanidipine, clevidipine, lercanidipine, or dilitiazem.

In another embodiment, the atrasentan mandelate salt may be co-administered with one or more renin inhibitors such as aliskiren (such as TEKTURNA™).

In another embodiment, the atrasentan mandelate salt may be co-administered with one or more aldosterone receptor antagonists such as eplerenone (such as INSPRA™) or spironolactone (such as ALDACTONE™).

In another embodiment, the atrasentan mandelate salt may be co-administered with one or more alpha blockers such as doxazosin (such as CARDURA™), phenoxybenzamine (such as DIBENZYLINE™), terazosin (such as HYTRIN™), CDRl-93/478, or CR-2991.

In another embodiment, the atrasentan mandelate salt may be co-administered with one or more beta blockers such as timolol (such as BLOCARDEN™), carteolol (such as CARTROL™), carvedilol (such as COREG™) nadolol (such as CORGARD™), propranolol (such as INNOPRAN XL™), betaxolol (such as KERLONE™), penbutolol (such as LEVATOL™), metoprolol (such as LOPRESSOR™ or TOPROL-XL™), atenolol (such as TENORMIN™), pindolol (such as VISKEN™), or bisoprolol.

In another embodiment, the atrasentan mandelate salt may be co-administered with one or more alpha-beta blockers such as labetalol (such as NORMODYNE™ or TRANDATE™).

In another embodiment, the atrasentan mandelate salt may be co-administered with one or more central antiadrenergics such as methyldopa (such as ALDOMET™), clonidine (such as CATAPRES™ or CATAPRES-TTS™), guanfacine (such as TENEX™), or guanabenz (such as WYTENSIN™).

In another embodiment, the atrasentan mandelate salt may be co-administered with one or more glycosides/inotropic agents such as digoxin (such as LANOXIN™)

In another embodiment, the atrasentan mandelate salt may be co-administered with one or more alpha glucosidase inhibitors, such as miglitol (such as GLYSET™) or acarbose (such as PRECOSE™)

In another embodiment, the atrasentan mandelate salt may be co-administered with one or more biguanides, such as rosiglitazone (such as AVANDAMET™) or metformin (such as GLUCOPHAGE™ or GLUCOPHAGE XR™)

In another embodiment, the atrasentan mandelate salt may be co-administered with one or more insulins, such as HUMALOG™, HUMALOG 50/50™, HUMALOG 75/25™, HUMULIN 50/50™, HUMALIN 75/25™ HUMALIN L™, HUMALIN N™, HUMALIN R™, HUMALIN R U-500™, HUMALIN U™, ILETIN II LENTE™, ILETIN II NPH™, ILETIN II REGULAR™, LANTUS™, NOVOLIN 70/30™, NOVILIN N™, NOVILIN R™, NOVOLOG™, or VELOSULIN BR™, and EXUBERA™.

In another embodiment, the atrasentan mandelate salt may be co-administered with one or more meglitnides, such as repaglinide (such as PRANDIN™) or nateglinide (such as STARLIX™).

In another embodiment, the atrasentan mandelate salt may be co-administered with one or more sulfonylureas, such as glimepiride (such as AMARYL™), glyburide (such as DIABETA™, GLYNASE PRESTAB™ or MICRONASE™), or glipizide (such as GLUCOTROL™, or GLUCOTROL XL™).

In another embodiment, the atrasentan mandelate salt may be co-administered with one or more thiazolidinediones, such as pioglitazone (such as ACTOS™) or rosiglitazone (such as AVANDIA™)

In another embodiment, the atrasentan mandelate salt may be co-administered with niacin or one or more nicotinic acid derivatives, such as NIACOR™, NIASPAN™, NICOLAR™, or SLO-NIACIN™.

In another embodiment, the atrasentan mandelate salt may be co-administered with one or more fabric acid derivatives, such as clofibrate (such as ATROMID-S™), gemfibrozil (such as LOPID™), or fenofibrate (such as TRICOR™).

In another embodiment, the atrasentan mandelate salt may be co-administered with one or more bile acid sequestrants, such as colestipol (such as COLESTID™), cholestyramine (such as LOCHOLEST™, PREVALITE™, QUESTRAN™, or QUESTRAN LIGHT™), or colesevelam (such as WELCHOL™)

In another embodiment, the atrasentan mandelate salt may be co-administered with one or more cholesterol absorption inhibitors, such as ezetimibe (such as ZETIA™).

In another embodiment, the atrasentan mandelate salt may be co-administered with one or more 3-hydroxy-3-methyl-glutaryl coenzyme A (HMG-CoA) reductase inhibitors (statins) such as fluvastatin (such as LESCOL™) atorvastatin (such as LIPITOR™), lovastatin (such as ALTOCOR™ or MEVACOR™), pravastatin (such as PRAVACHOL™), rosuvastatin (such as CRESTOR™), or simvastatin (such as ZOCOR™).

In another embodiment, the present disclosure relates to the use of a pharmaceutical composition comprising an atrasentan mandelate salt for treating a condition as described in the various embodiments of the disclosure.

In another embodiment, the present disclosure relates to the use of a first pharmaceutical composition in combination with a second pharmaceutical composition for treating a condition as described in the various embodiments of the disclosure, wherein the first pharmaceutical composition comprises an atrasentan mandelate salt, and the second pharmaceutical composition comprises a second therapeutic agent.

In another embodiment, the present disclosure relates to the use of a pharmaceutical composition comprising an atrasentan mandelate salt for treating a condition as described in the various embodiments of the disclosure, wherein the pharmaceutical composition further comprises one or more additional therapeutic agents.

In another embodiment, the present disclosure relates to a pharmaceutical composition comprising an atrasentan mandelate salt, and further comprising a second therapeutic agent. In one aspect, the second therapeutic agent inhibits one or more elements of the renin-angiotensin-aldosterone system. In a further aspect, the second therapeutic agent is selected from the group consisting of diuretics, angiotensin converting enzyme inhibitors, angiotensin II receptor blockers, calcium channel blockers, renin inhibitors, and aldosterone antagonists. In a further aspect, the second therapeutic agent is selected from the group consisting of angiotensin converting enzyme inhibitors and angiotensin II receptor blockers. In a further aspect, the second therapeutic agent is an angiotensin converting enzyme inhibitor. In a further aspect, the second therapeutic agent is an angiotensin II receptor blocker.

VI. Kits

The present disclosure also relates to kits comprising one or more solid pharmaceutical dosage forms (such as tablets or capsules) comprising an atrasentan mandelate salt. The kit optionally can comprise one or more additional therapeutic agents and/or instructions, for example, instructions for using the kit.

In one embodiment, the kit comprises a semi-permeable container containing one or more solid pharmaceutical dosage forms comprising an atrasentan mandelate salt. In one aspect, the semi-permeable container is a blister pack.

In another embodiment, the kit comprises a substantially impermeable container containing one or more solid pharmaceutical dosage forms comprising an atrasentan mandelate salt.

In another embodiment, the kit comprises a first dosage form and a second dosage form, wherein the first dosage form is a solid pharmaceutical dosage form comprising an atrasentan mandelate salt, and the second dosage form comprises a second therapeutic agent. In a further aspect, the second therapeutic agent is selected from the group consisting of diuretics, angiotensin converting enzyme inhibitors, angiotensin II receptor blockers, calcium channel blockers, renin inhibitors, and aldosterone antagonists. In a further aspect, the second therapeutic agent is selected from the group consisting of angiotensin converting enzyme inhibitors and angiotensin II receptor blockers. In a further aspect, the second therapeutic agent is an angiotensin converting enzyme inhibitor. In a further aspect, the second therapeutic agent is an angiotensin II receptor blocker. In a further aspect, the kit comprises a semi-permeable container containing the first dosage form and the second dosage form. In a further aspect, the kit comprises a blister pack containing the first dosage form and the second dosage form. In a further aspect, the kit comprises an impermeable container containing the first dosage form and the second dosage form.

VII. Methods of Preparation

The present disclosure also relates to methods for preparing an atrasentan mandelate salt, wherein the method comprises the steps of (a) contacting atrasentan with a solvent comprising mandelic acid to form a mixture comprising an atrasentan mandelate salt, and (b) isolating the atrasentan mandelate salt from the mixture. In one embodiment, the molar ratio of mandelic acid to atrasentan in the contacting step is greater than about 1:1. In another embodiment, the isolated salt is a crystalline salt such as an anhydrous crystalline salt. In another embodiment, the molar ratio of mandelic acid to atrasentan in the contacting step is greater than about 1:1, and the isolated salt is a crystalline salt such as an anhydrous crystalline salt. In one embodiment, the mandelic acid is S-mandelic acid. In another embodiment, the mandelic acid is R-mandelic acid. In another embodiment, the contacting step optionally comprises heating the mixture to substantially dissolve any solids present.

In another embodiment, the contacting step optionally comprises stirring or agitating the mixture. In another embodiment, the isolation step optionally comprises cooling the mixture. In another embodiment, the isolation step optionally comprises filtering the mixture.

The solvent selected can be a single solvent or a mixture of two or more different solvents. In one embodiment, the solvent comprises water. In another embodiment the solvent comprises methanol. In another embodiment, the solvent comprises water and methanol. In another embodiment, the solvent is a 1:1 volume to volume mixture of water and methanol. In another embodiment, the solvent comprises at least one member selected from the group consisting of acetonitrile, ethanol, and pyridine.

Crystallization/precipitation of the salt can be facilitated as needed by methods such as cooling, seeding, partial removal of the solvent from the atrasentan/solvent solution, addition of an anti-solvent to the atrasentan/solvent solution, or combinations of such methods. In one embodiment, the atrasentan/solvent solution is seeded with the desired crystalline atrasentan mandelate salt, such as an anhydrous crystalline atrasentan S-mandelate salt having a molar ratio of atrasentan to S-mandelate of about 1:1.

The mandelate salt can be isolated using conventional isolation methods such as filtration, filtration under vacuum or pressure, decantation, centrifugation, manual separation, or a combination of those methods.

The isolated mandelate salt can be further dried in, for example, a vacuum tray dryer, Rotocon vacuum dryer, vacuum paddle dryer, or pilot plant Rota vapor, to further lower residual solvents. Drying can be carried out under reduced pressure until the residual solvent content is reduced to the desired amount (such as an amount that is within the limits of applicable International Conference on Harmonization guidelines.

Where the desired salt is an atrasentan S-mandelate salt having a molar ratio of atrasentan to S-mandelate of about 1:1, the method may employ a molar excess of mandelic acid in the contacting step, particularly where the use of a lower amount of mandelic acid results in a mixture of atrasentan S-mandelate salts (e.g., a mixture of one salt having a molar ratio of atrasentan to S-mandelate of about 1:1 and a second salt having a molar ratio of atrasentan to S-mandelate of about 2:1). Accordingly, in one embodiment, the molar ratio of mandelic acid to atrasentan in the contacting step is at least about 2:1. In another embodiment, the molar ratio of mandelic acid to atrasentan in the contacting step is at least about 3:1. In another embodiment, the molar ratio of mandelic acid to atrasentan in the contacting step is at least about 4:1.

In one embodiment, the isolated salt comprises at least about 95 weight percent of atrasentan S-mandelate salt having a molar ratio of atrasentan to S-mandelate of about 1:1. In another aspect, the weight percent is at least about 96 weight percent. In another aspect, the weight percent is at least about 97 weight percent. In another aspect, the weight percent is at least about 98 weight percent. In another aspect, the weight percent is at least about 99 weight percent. In another aspect, the isolated salt is substantially atrasentan S-mandelate salt having a molar ratio of atrasentan to S-mandelate of about 1:1.

In another embodiment, the isolated salt comprises at least about 95 weight percent of crystalline atrasentan S-mandelate salt and has a crystalline purity of at least about 90 percent with respect to crystalline atrasentan S-mandelate salt having a molar ratio of atrasentan to S-mandelate of about 1:1. In another aspect, the weight percent is at least about 96 weight percent and the crystalline purity is at least 93 percent. In another aspect, the weight percent is at least about 97 weight percent and the crystalline purity is at least 95 percent. In another aspect, the weight percent is at least about 98 weight percent and the crystalline purity is at least 97 percent. In another aspect, the weight percent is at least about 99 weight percent and the crystalline purity is at least 99 percent. In another aspect, the isolated salt is substantially anhydrous crystalline atrasentan S-mandelate salt having a molar ratio of atrasentan to S-mandelate of about 1:1.

VIII. Product-By-Process

The present disclosure also relates to atrasentan mandelate salts prepared in accordance with any of the methods described in the disclosure.

IX. Examples

Example 1

Atrasentan Salts

Several studies were conducted to identify new atrasentan salts (particularly new crystalline atrasentan salts) and are described below.

A. Experiment A

Solutions of several different organic or inorganic acids in a methanol solvent were prepared for use in the study. These solutions (including their concentrations) are reported in Table 1-A below.

TABLE 1-A

| SALT FORMING AGENT | SOLVENT | CONC. (M) | VOLUME (µL) | PRECIPITATION |
|---|---|---|---|---|
| $H_2SO_4$ | Methanol | 1 | 100 | Yes (amorphous) |
| $H_3PO_4$ | Methanol | 1 | 100 | No |
| Citric acid | Methanol | 0.5 | 200 | No |
| L-Tartaric acid | Methanol | 0.5 | 200 | No |
| Malonic acid | Methanol | 0.5 | 200 | No |
| Succinic acid | Methanol | 0.5 | 200 | No |
| Glycolic acid | Methanol | 0.5 | 200 | No |
| L-Malic acid | Methanol | 0.5 | 200 | No |
| S-Mandelic acid | Methanol | 0.5 | 200 | Yes (gel-like semi-solid) |

Each acid/methanol solution prepared was added with stirring to a vial containing 25 mg of atrasentan parent dissolved completely in 100 µL of methanol. Each addition was carried out at room temperature and the volume of acid/methanol solution added to the vial is reported in Table 1-A.

A solid precipitate resulted from the $H_2SO_4$/methanol addition. The precipitate was isolated and determined to be an amorphous solid.

A gel-like semi-solid precipitate resulted from the S-mandelic acid/methanol addition. The solution containing the precipitate was stirred for at least one week, but the precipitate remained a gel-like semi-solid.

No precipitation was observed for any of the other acid/solvent additions. For each addition where no precipitation was observed, the vial was covered with parafilm having two pin-holes and the solution was allowed to slowly evaporate. An amorphous film was observed in each vial after the solution was completely dried.

No crystalline atrasentan salts were successfully prepared and isolated.

B. Experiment B

Aqueous solutions of several different organic or inorganic acids (including a methanol/water solution for one acid) were prepared for use in the study. These solutions (including their concentrations) are reported in Table 1-B below.

TABLE 1-B

| SALT FORMING AGENT | SOLVENT | CONC. (M) | VOLUME (µL) | PRECIPITATION |
|---|---|---|---|---|
| $H_2SO_4$ | Water | 1 | 400 | Yes (crystalline) |
| $H_3PO_4$ | Water | 1 | 300 | Yes (gel-like semi-solid) |
| Citric acid | Water | 1 | 200 | Yes (gel-like semi-solid) |
| L-Tartaric acid | Water | 1 | 200 | Yes (gel-like semi-solid) |
| Malonic acid | Water | 1 | 200 | Yes (gel-like semi-solid) |
| Succinic acid | Methanol/Water (1:1, v/v) | 1 | 200 | Yes (gel-like semi-solid) |
| Glycolic acid | $H_2O$ | 1 | 200 | Yes (gel-like semi-solid) |
| L-Malic acid | $H_2O$ | 1 | 200 | Yes (gel-like semi-solid) |
| S-Mandelic acid | $H_2O$ | 0.5 | 200 | Yes (gel-like semi-solid) |
| R-Mandelic acid | $H_2O$ | 0.5 | 200 | Yes (gel-like semi-solid) |

Each aqueous solution prepared was added with stirring to a vial containing 25 mg of atrasentan parent dissolved completely in 100 µL of 2-propanol/water (80/20, v/v). Each addition was carried out at room temperature and the volume of the aqueous solution added to the vial is reported in Table 1-B.

A solid precipitate resulted from the $H_2SO_4$/water addition. The precipitate was isolated as a crystalline solid and determined to be a monohydrate of the atrasentan hemi-sulfate salt (1:1 molar ratio of atrasentan to sulfate).

A gel-like semi-solid precipitate resulted from all of the other aqueous solution additions. Each solution was then heated to 70° C. to re-dissolve the semi-solid precipitate. In several cases, up to 25 µL of additional 2-propanol/water (80/20, v/v) was added to the vial as needed to completely re-dissolve the semi-solid precipitate. After the semi-solid precipitate was re-dissolved, each solution was cooled slowly to room temperature. A gel-like semi-solid was observed at the bottom of each vial within 10 hours.

Except for the monohydrate of the hemi-sulfate salt, no other crystalline atrasentan salts were successfully prepared and isolated.

C. Experiment C

Aqueous solutions of several different organic or inorganic acids (or a methanol/water solution for one acid) and an aqueous solution of nicotinamide were prepared for use in the study. These solutions (including their concentrations) are reported in Table 1-C below.

TABLE 1-C

| SALT FORMING AGENT | SOLVENT | CONC. (M) | VOLUME (µL) | REMAINED AS PARENT? |
|---|---|---|---|---|
| H₃PO₄ | Water | 1 | 1000 | Yes |
| Citric acid | Water | 1 | 1000 | Yes |
| L-Tartaric acid | Water | 1 | 1000 | Yes |
| Malonic acid | Water | 1 | 1000 | Yes |
| Succinic acid | Methanol/Water (1:1, v/v) | 1 | 1000 | Yes |
| Glycolic acid | Water | 1 | 1000 | Yes |
| L-Malic acid | Water | 1 | 1000 | Yes |
| S-Mandelic acid | Water | 0.5 | 1000 | Yes |
| R-Mandelic acid | Water | 0.5 | 1000 | Yes |
| Nicotinamide | Water | 1 | 1000 | Yes |

About 52 mg of atrasentan parent was suspended in 1 mL of each aqueous solution prepared and the resulting suspensions were stirred for three to seven days. The solids isolated from each suspension were analyzed and determined to be the atrasentan parent solid.

No crystalline atrasentan salts or co-crystals were successfully prepared and isolated.

D. Experiment D

Aqueous solutions of several different organic or inorganic acids (or a methanol/water solution for one acid) were prepared for use in the study. These solutions (including their concentrations) are reported in Table 1-D below.

TABLE 1-D

| SALT FORMING AGENT | SOLVENT | CONC. (M) | VOL. (µL) | OBSERVATIONS |
|---|---|---|---|---|
| H₃PO₄ | Water | 1 | 400 | Good suspension |
| Citric acid | Water | 1 | 300 | Agglomerated |
| Glycolic acid | Water | 1 | 200 | Good suspension |
| L-Lactic acid | Water | 1 | 200 | Good suspension |
| L-Malic acid | Water | 1 | 200 | Good suspension |
| Malonic acid | Water | 1 | 200 | Gelled up |
| Succinic acid | Methanol/Water (1:1, v/v) | 0.5 | 200 | Good suspension |
| L-Tartaric acid | Water | 1 | 200 | Good suspension |
| S-Mandelic acid | Water | 0.5 | 200 | Gelled up |
| R-Mandelic acid | Water | 0.5 | 200 | Gelled up |

Each aqueous solution prepared was added with stirring to a 4 mL vial containing 50 mg of atrasentan parent in solid form. The additions were carried out at room temperature and the volume of the aqueous solution added to the vial is reported in Table 1-D. The atrasentan only partially dissolved in each aqueous solution. The resulting suspensions were stirred for more than a week. The solids isolated from each suspension were analyzed and determined to be the atrasentan parent.

No crystalline atrasentan salts were successfully prepared and isolated.

E. Experiment E

Atrasentan parent was added to an aqueous sodium hydroxide solution. The solution turned pink immediately upon the addition of the atrasentan and no sodium salt of atrasentan was isolated. Because atrasentan generally degrades under basic conditions, it is believed that the atrasentan degraded in the presence of the sodium hydroxide and was not converted into a sodium salt.

Example 2

Atrasentan S-Mandelate Salt

Several additional studies were conducted to prepare and isolate atrasentan S-mandelate (particularly crystalline atrasentan S-mandelate) and are described below.

A. Experiment A

About 25 mg of atrasentan parent was suspended in 0.2 mL of an aqueous solution of S-mandelic acid (0.5 M) at room temperature. The suspended solid quickly converted to a gel-like semi-solid when the solution was stirred. After three days of stirring at room temperature, a sample of the suspended semi-solid was inspected under microscope and a few birefringent particles were observed.

B. Experiment B

About 22 mg of atrasentan parent was suspended in 0.25 mL of methanol/water (50/50, v/v) at room temperature. S-Mandelic acid (13.8 mg) was added to the suspension. The suspended solids partially dissolved in the S-mandelic acid and were converted quickly to a gel-like semi-solid. The solution was heated to 40° C. and the semi-solid was re-dissolved. The solution was then slowly cooled to room temperature and produced a solid precipitate. The precipitate was isolated, analyzed by PXRD, and determined to be a mixture of an anhydrate of atrasentan S-mandelate (1:1 stoichiometry) and a hemi-hydrate of atrasentan parent.

C. Experiment C

About 100 mg of atrasentan parent was suspended in 1 mL of methanol/water (1:1, v/v) at room temperature. S-Mandelic acid (41 mg) was added to the suspension. The majority of the suspended solids dissolved, but a gel-like semi-solid was observed at the bottom of the vial. The suspension was heated to 50° C., but the semi-solid remained undissolved. When the suspension was stirred for 10 minutes at 50° C., additional precipitation was observed. When the suspension was stirred overnight, the semi-solid partially converted to crystalline particles. A sample of the crystalline particles was analyzed by PXRD and determined to be a mixture of an anhydrate of atrasentan S-mandelate (1:1 stoichiometry) and an anhydrate of atrasentan S-mandelate (2:1 stoichiometry). Additional S-mandelic acid (about 15 mg) was added to the suspension with stirring to further convert the semi-solid to crystalline particles. The resulting crystalline particles were isolated, analyzed by PXRD, and determined to be an anhydrate of atrasentan S-mandelate (1:1 stoichiometry). Increasing the amount of S-mandelic acid present in the suspension resulted in the conversion of the atrasentan S-mandelate (2:1 stoichiometry) to atrasentan S-mandelate (1:1 stoichiometry).

D. Experiment D

About 500 mg of atrasentan parent was dissolved in 2.5 mL methanol at room temperature. S-Mandelic acid (315 mg) was added to the solution. Water was gradually added to the solution in increments of 0.1 mL (to reduce solubility and facilitate precipitation). After a total of 1.5 mL of water had been added to the solution, precipitation of fine particles was observed. An additional amount of S-mandelic acid (about 150 mg) was added to the suspension after 10 minutes followed by an additional amount of water (1 mL). The suspension was then stirred for three hours. The solids present in the suspension were isolated, analyzed by PXRD, and determined to be an anhydrate of atrasentan S-mandelate (1:1 stoichiometry).

E. Experiment E

About 22 mg of atrasentan parent was suspended in 0.25 mL of a methanol/water (1/1, v/v) mixture in a 1 mL scintillation vial at room temperature with stirring. After 9.8 mg of S-mandelic acid had been added to the suspension, the atrasentan was completely dissolved and a semi-solid agglomerate appeared at the bottom of the vial shortly afterwards. The mixture was stirred continuously overnight and the semi-solid agglomerate turned into a white solid that was suspended in the solution. The solid was isolated by filtration and analyzed by PXRD. The PXRD data indicated the solid was a combination of at least two different crystalline forms.

Example 3

Crystallization of Atrasentan S-Mandelate Salt from Additional Solvents

A. Crystallization From Acetonitrile

An excess amount of S-mandelic acid was suspended in acetonitrile (1 mL) to prepare a saturated S-mandelic acid/acetonitrile solution. After saturation was achieved, the excess S-mandelic acid was removed from the solution by filtration. An excess amount of atrasentan S-mandelate salt (1:1 stoichiometry) was suspended in the S-mandelic acid/acetonitrile solution at room temperature for three days with stirring. The resulting solid was isolated by filtration and analyzed by PXRD about 10 minutes after isolation (see Example 8).

B. Crystallization From Ethanol

An excess amount of S-mandelic acid was suspended in ethanol (1 mL) to prepare a saturated S-mandelic acid/acetonitrile solution. After saturation was achieved, the excess S-mandelic acid was removed from the solution by filtration. An excess amount of atrasentan S-mandelate salt (1:1 stoichiometry) was suspended in the S-mandelic acid/ethanol solution at room temperature for three days with stirring. The resulting solid was isolated by filtration and analyzed by PXRD about 10 minutes after isolation (see Example 8).

C. Crystallization From Pyridine

An excess amount of S-mandelic acid was suspended in pyridine (1 mL) to prepare a saturated S-mandelic acid/pyridine solution. After saturation was achieved, the excess S-mandelic acid was removed from the solution by filtration. An excess amount of atrasentan S-mandelate salt (1:1 stoichiometry) was suspended in the S-mandelic acid/ethanol solution at room temperature for three days with stirring. The resulting solid was isolated by filtration and analyzed by PXRD about 10 minutes after isolation (see Example 8).

Example 4

Atrasentan S-Mandelate Salt (2:1 Stoichiometry)

100.6 mg of atrasentan parent was suspended in 1 mL of a methanol/water (1/1, v/v) mixture in a 4 mL scintillation vial at 50° C. with stirring. A semi-solid agglomerate appeared at the bottom of the vial after 31 mg of S-mandelic acid had been added to the suspension. The mixture was stirred continuously for 15 minutes and then the semi-solid agglomerate turned into a white solid that was suspended in the solution. The solid was isolated by filtration and analyzed by PXRD (see Example 8). The solid was found to be a hydrate of atrasentan S-mandelate salt (2:1 stoichiometry).

Example 5

Atrasentan R-Mandelate Salt (1:1 Stoichiometry)

About 100 mg of atrasentan parent was added to about 1 mL of an R-mandelic acid/water solution (0.5 M) at room temperature. A gel-like precipitate was observed in the resulting suspension. The suspension was sonicated for 15 minutes and heated to 50° C. with stirring. As the suspension was stirred and the temperature maintained at 50° C., the gel-like precipitate converted to a white solid. The white solid was isolated, dried, analyzed by PXRD (see Example 8), and determined to be an anhydrate of atrasentan R-mandelate (1:1 stoichiometry).

Example 6

Atrasentan n-Butylamine Salt (1:1 Stoichiometry)

Atrasentan monohydrochloride (11.42 mg) was added to a 2 mL glass vial containing a mixture of n-butylamine (100 µL) and isopropanyl acetate (400 µL) and dissolved by vortexing. A crystalline solid of was collected after the solvent was removed by evaporation under ambient conditions. The crystalline solid was analyzed by PXRD (see Example 8) and determined to be an anhydrate of atrasentan n-butylamine (1:1 stoichiometry).

Although the atrasentan n-butylamine salt was successfully isolated, n-butylamine is generally toxic and an n-butylamine salt is not a pharmaceutically acceptable salt.

Example 7

Crystal Morphology

The crystal morphology of several different atrasentan salts was assessed by microscopy and the results reported in Table 7-A below.

TABLE 7-A

| ATRASENTAN SALT | ANALYTICAL CHARACTERIZATION | CRYSTAL MORPHOLOGY |
|---|---|---|
| Parent | Anhydrate | Needle |
| Parent | Quarter-hydrate | Needle |
| Parent | Hemi-hydrate | Prism |
| Hemi-Sulfate (1:1 Stoichiometry) | Monohydrate (Example 1, Experiment 2) | Needle |
| S-Mandelate (1:1 Stoichiometry) | Anhydrate (Example 2, Experiment 4) | Prism |
| S-Mandelate (1:1 Stoichiometry) | Crystallized From Acetonitrile (Example 3) | Prism |
| S-Mandelate (1:1 Stoichiometry) | Crystallized From Ethanol (Example 3) | Not Determined |
| S-Mandelate (1:1 Stoichiometry) | Crystallized From Pyridine (Example 3) | Not Determined |
| S-Mandelate (2:1 Stoichiometry) | Hydrate (Example 4) | Prism |
| R-Mandelate (1:1 Stoichiometry) | Anhydrate (Example 5) | Prism |
| n-Butylamine (1:1 Stoichiometry) | Anhydrate (Example 6) | Bar |
| Hydrochloride (1:1 Stoichiometry) | Crystalline Form I (Reported in WO2006/034094) | Needle |
| Hydrochloride (1:1 Stoichiometry) | Crystalline Form II (Reported in WO2006/034084) | Needle |
| Hydrochloride (1:1 Stoichiometry) | Crystalline Form III (Reported in WO2006/034234) | Needle |

Microscopic images of (a) atrasentan hemi-sulfate (1:1 stoichiometry), monohydrate, (b) atrasentan S-mandelate salt (1:1 stoichiometry), anhydrate, and (c) atrasentan monohydrochloride salt, crystalline Form II are attached as FIG. 1-A, FIG. 1-B, and FIG. 1-C, respectively.

Example 8

PXRD Analysis of Crystalline Atrasentan Salts

Several of the atrasentan crystalline forms listed in Table 7-A were analyzed by X-ray powder diffraction ("PXRD"). Specifically, the PXRD studies were performed on a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromator provided monochromatic K$\alpha$1 radiation. The diffractometer was calibrated using the attenuated direct beam at one-degree intervals. Calibration was checked using a silicon powder line position reference standard (NIST 640c). The sample was loaded onto an aluminum sample holder and leveled with a glass slide. The instrument was computer controlled using the Symphonix software (Inel Corp., Artenay, France) and the data was analyzed using the Jade software (version 6.5, Materials Data, Inc., Livermore, Calif.). All studies were conducted at room temperature (i.e., about 25° C.).

Tables 8-A through 8-N set out the significant parameters of the main peaks in terms of 2Θ values and intensities for the crystalline forms analyzed. It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realize that the relative intensities of peaks may vary according to the orientation of the sample under testing and on the type and setting of the instrument used. The skilled person also will realize that the position of reflections can be affected by the precise height at which the sample sits in the diffractometer and the zero calibration of the diffractometer. The surface planarity of the sample also may have an effect on the results. A person skilled in the art will appreciate that the diffraction pattern data presented below is not to be construed as absolute and any crystalline form that provides a power diffraction pattern substantially identical to those disclosed below fall within the scope of the present disclosure (for further information see Jenkins, R & Snyder, R. L. 'Introduction to X-Ray Powder Diffractometry' John Wiley & Sons, 1996).

TABLE 8-A

PXRD Peak Listing
Hemi-Sulfate Salt (1:1 Stoichiometry), Monohydrate

| PEAK POSITION (°2Θ) | RELATIVE INTENSITY |
|---|---|
| 5.5 | 100.0 |
| 7.3 | 7.1 |
| 8.3 | 31.8 |
| 11.0 | 2.1 |
| 11.8 | 1.8 |
| 13.1 | 3.7 |
| 16.0 | 4.4 |
| 16.5 | 11.0 |
| 16.8 | 13.7 |
| 17.1 | 7.4 |
| 19.0 | 7.2 |
| 19.3 | 9.1 |
| 19.8 | 7.1 |
| 22.1 | 9.1 |
| 23.8 | 13.8 |
| 25.8 | 9.1 |

The PXRD pattern corresponding to the data reported in Table 8-A is graphically shown in FIG. 2-A.

TABLE 8-B

PXRD Peak Listing
S-Mandelate Salt (1:1 Stoichiometry), Anhydrate

| PEAK POSITION (°2Θ) | RELATIVE INTENSITY |
|---|---|
| 5.5 | 100.0 |
| 8.4 | 7.3 |
| 9.1 | 10.9 |
| 9.7 | 62.9 |
| 10.3 | 12.8 |
| 11.2 | 2.5 |
| 11.8 | 4.8 |
| 12.1 | 51.5 |
| 13.7 | 12.0 |
| 14.2 | 11.3 |
| 16.1 | 26.2 |
| 16.3 | 23.7 |
| 17.7 | 14.1 |
| 18.0 | 37.5 |
| 18.4 | 37.0 |
| 19.4 | 94.6 |
| 20.0 | 26.5 |
| 20.6 | 10.7 |
| 20.8 | 33.1 |
| 21.2 | 23.2 |
| 22.3 | 20.1 |
| 23.0 | 37.7 |
| 23.9 | 20.8 |
| 24.2 | 17.3 |

The PXRD pattern corresponding to the data reported in Table 8-B is graphically shown in FIG. 2-B.

TABLE 8-C

PXRD Peak Listing
S-Mandelate Salt (1:1 Stoichiometry)-Crystallized From Acetonitrile

| PEAK POSITION (°2Θ) | RELATIVE INTENSITY |
|---|---|
| 6.0 | 100.0 |
| 7.7 | 0.6 |
| 9.0 | 1.8 |
| 9.2 | 0.6 |
| 10.0 | 6.6 |
| 12.1 | 1.8 |
| 12.5 | 1.8 |
| 13.9 | 8.6 |
| 14.4 | 8.7 |
| 15.7 | 3.5 |
| 16.1 | 2.5 |
| 16.4 | 2.4 |
| 17.5 | 9.1 |
| 18.3 | 4.9 |
| 20.2 | 2.0 |
| 21.0 | 5.5 |
| 23.8 | 7.6 |

The PXRD pattern corresponding to the data reported in Table 8-C is graphically shown in FIG. 2-C.

TABLE 8-D

PXRD Peak Listing
S-MandelateSalt (1:1 Stoichiometry)-Crystallized From Ethanol

| PEAK POSITION (°2Θ) | RELATIVE INTENSITY |
|---|---|
| 6.0 | 100.0 |
| 6.7 | 10.2 |
| 8.4 | 30.3 |
| 9.6 | 2.2 |
| 12.1 | 35.8 |
| 13.0 | 10.3 |
| 13.6 | 15.4 |
| 15.6 | 9.4 |
| 16.9 | 5.4 |
| 18.5 | 8.9 |
| 19.4 | 6.4 |
| 20.3 | 6.2 |
| 20.5 | 6.2 |
| 21.1 | 13.1 |
| 21.6 | 7.6 |
| 22.1 | 8.9 |
| 22.8 | 5.6 |

The PXRD pattern corresponding to the data reported in Table 8-D is graphically shown in FIG. 2-D.

TABLE 8-E

PXRD Peak Listing
S-MandelateSalt (1:1 Stoichiometry)-Crystallized From Pyridine

| PEAK POSITION (°2Θ) | RELATIVE INTENSITY |
|---|---|
| 6.7 | 17.2 |
| 11.6 | 22.4 |
| 13.0 | 9.6 |
| 13.4 | 8.7 |
| 15.0 | 4.6 |
| 16.9 | 2.0 |
| 17.4 | 17.9 |
| 18.5 | 1.5 |
| 19.1 | 3.2 |
| 20.2 | 100.0 |
| 21.6 | 3.9 |
| 22.4 | 14.4 |
| 22.6 | 19.3 |
| 23.4 | 12.0 |

The PXRD pattern corresponding to the data reported in Table 8-E is graphically shown in FIG. 2-E.

TABLE 8-F

PXRD Peak Listing
S-Mandelate Salt (2:1 Stoichiometry), Hydrate

| PEAK POSITION (°2Θ) | RELATIVE INTENSITY |
|---|---|
| 4.5 | 100.0 |
| 6.7 | 5.9 |
| 8.2 | 7.3 |
| 8.6 | 84.8 |
| 9.1 | 27.5 |
| 9.5 | 19.5 |
| 10.7 | 19.4 |
| 11.7 | 13.2 |
| 12.3 | 17.6 |
| 13.4 | 14.9 |
| 14.1 | 19.9 |
| 17.2 | 15.0 |
| 17.4 | 15.1 |
| 18.1 | 95.1 |
| 18.5 | 19.4 |
| 18.7 | 73.5 |
| 19.2 | 16.1 |
| 19.6 | 12.2 |

TABLE 8-F-continued

PXRD Peak Listing
S-Mandelate Salt (2:1 Stoichiometry), Hydrate

| PEAK POSITION (°2Θ) | RELATIVE INTENSITY |
|---|---|
| 20.3 | 13.4 |
| 20.7 | 17.9 |
| 21.6 | 24.5 |
| 22.0 | 15.1 |
| 24.0 | 15.3 |
| 24.2 | 12.3 |

The PXRD pattern corresponding to the data reported in Table 8-F is graphically shown in FIG. 2-F.

TABLE 8-G

PXRD Peak Listing
R-Mandelate Salt (1:1 Stoichiometry), Anhydrate

| PEAK POSITION (°2Θ) | RELATIVE INTENSITY |
|---|---|
| 5.7 | 100.0 |
| 8.2 | 32.7 |
| 8.6 | 25.3 |
| 10.1 | 16.7 |
| 11.5 | 15.3 |
| 11.8 | 49.0 |
| 16.2 | 42.7 |
| 16.4 | 12.1 |
| 16.8 | 18.5 |
| 18.4 | 28.1 |
| 18.7 | 47.1 |
| 19.3 | 36.5 |
| 20.2 | 16.3 |
| 20.9 | 62.4 |
| 21.8 | 10.0 |
| 23.4 | 26.4 |
| 24.7 | 18.7 |
| 25.3 | 20.7 |

The PXRD pattern corresponding to the data reported in Table 8-G is graphically shown in FIG. 2-G.

TABLE 8-H

PXRD Peak Listing
n-Butylamine Salt (1:1 Stoichiometry), Anhydrate

| PEAK POSITION (°2Θ) | RELATIVE INTENSITY |
|---|---|
| 5.4 | 2.9 |
| 7.6 | 100.0 |
| 7.8 | 83.9 |
| 8.5 | 4.0 |
| 8.7 | 4.9 |
| 10.9 | 40.1 |
| 13.8 | 14.5 |
| 14.3 | 88.2 |
| 14.8 | 68.8 |
| 15.2 | 23.9 |
| 17.6 | 40.3 |
| 17.9 | 23.2 |
| 18.3 | 97.4 |
| 18.5 | 25.4 |
| 19.5 | 20.6 |
| 20.0 | 65.8 |
| 20.9 | 35.9 |
| 21.3 | 33.0 |
| 22.0 | 37.0 |
| 22.3 | 38.7 |
| 22.7 | 43.4 |
| 23.7 | 21.4 |
| 23.9 | 25.5 |

TABLE 8-H-continued

PXRD Peak Listing
n-Butylamine Salt (1:1 Stoichiometry), Anhydrate

| PEAK POSITION (°2Θ) | RELATIVE INTENSITY |
|---|---|
| 24.3 | 23.7 |
| 24.8 | 50.7 |

The PXRD pattern corresponding to the data reported in Table 8-H is graphically shown in FIG. 2-H.

TABLE 8-I

PXRD Peak Listing
Parent, Anhydrate

| PEAK POSITION (°2Θ) | RELATIVE INTENSITY |
|---|---|
| 1.305 | 6.7 |
| 1.634 | 5.5 |
| 7.168 | 25.5 |
| 8.759 | 16.0 |
| 11.314 | 100.0 |
| 12.142 | 7.4 |
| 14.327 | 20.2 |
| 15.002 | 19.2 |
| 15.638 | 11.5 |
| 16.457 | 8.4 |
| 17.388 | 86.8 |
| 19.625 | 5.4 |
| 19.986 | 11.6 |
| 20.151 | 28.6 |
| 20.469 | 7.8 |
| 20.929 | 41.7 |
| 21.575 | 51.5 |
| 22.750 | 15.3 |
| 23.161 | 14.4 |
| 23.773 | 14.9 |
| 24.816 | 9.1 |
| 26.382 | 17.8 |

The PXRD pattern corresponding to the data reported in Table 8-I is graphically shown in FIG. 2-I.

TABLE 8-J

PXRD Peak Listing
Parent, Quarter-Hydrate

| PEAK POSITION (°2Θ) | RELATIVE INTENSITY |
|---|---|
| 3.7 | 100.0 |
| 7.5 | 7.1 |
| 8.4 | 32.1 |
| 9.9 | 22.0 |
| 10.2 | 4.0 |
| 11.2 | 2.5 |
| 12.0 | 6.1 |
| 13.4 | 4.2 |
| 14.1 | 5.2 |
| 16.4 | 9.5 |
| 16.7 | 6.6 |
| 18.0 | 23.3 |
| 18.5 | 30.0 |
| 19.5 | 9.5 |
| 22.2 | 16.6 |
| 22.6 | 35.7 |
| 24.8 | 13.2 |
| 25.8 | 15.6 |

The PXRD pattern corresponding to the data reported in Table 8-J is graphically shown in FIG. 2-J.

TABLE 8-K

PXRD Peak Listing
Parent, Hemi-Hydrate

| PEAK POSITION (°2Θ) | RELATIVE INTENSITY |
|---|---|
| 3.6 | 100.0 |
| 8.6 | 8.5 |
| 8.9 | 8.8 |
| 9.1 | 6.6 |
| 9.3 | 2.9 |
| 10.0 | 8.0 |
| 10.7 | 4.6 |
| 10.9 | 6.0 |
| 12.2 | 9.2 |
| 13.1 | 6.8 |
| 14.9 | 3.8 |
| 15.2 | 4.5 |
| 15.5 | 3.1 |
| 16.0 | 16.4 |
| 17.3 | 3.0 |
| 17.7 | 8.4 |
| 18.0 | 9.0 |
| 18.3 | 9.4 |
| 19.6 | 12.8 |
| 20.2 | 6.3 |
| 21.3 | 30.0 |
| 21.9 | 23.2 |

The PXRD pattern corresponding to the data reported in Table 8-K is graphically shown in FIG. 2-K.

TABLE 8-L

PXRD Peak Listing
Monohydrochloride Salt, Crystalline Form I

| PEAK POSITION (°2Θ) | RELATIVE INTENSITY |
|---|---|
| 8.3 | 100.0 |
| 9.7 | 97.9 |
| 10.1 | 58.9 |
| 10.9 | 27.5 |
| 11.8 | 7.0 |
| 12.1 | 8.3 |
| 13.1 | 75.6 |
| 13.5 | 25.9 |
| 14.8 | 20.2 |
| 15.7 | 46.7 |
| 16.1 | 22.0 |
| 16.7 | 42.4 |
| 17.2 | 46.6 |
| 17.5 | 22.8 |
| 19.5 | 47.7 |
| 20.2 | 11.0 |
| 20.7 | 26.8 |
| 21.8 | 11.4 |
| 22.6 | 33.5 |
| 23.2 | 29.2 |
| 24.2 | 27.6 |

The PXRD pattern corresponding to the data reported in Table 8-L is graphically shown in FIG. 2-L.

TABLE 8-M

PXRD Peak Listing
Monohydrochloride Salt, Crystalline Form II

| PEAK POSITION (°2Θ) | RELATIVE INTENSITY |
|---|---|
| 8.3 | 100.0 |
| 9.7 | 97.9 |
| 10.1 | 58.9 |
| 10.9 | 27.5 |
| 13.1 | 75.6 |
| 13.5 | 25.9 |

TABLE 8-M-continued

PXRD Peak Listing
Monohydrochloride Salt, Crystalline Form II

| PEAK POSITION (°2Θ) | RELATIVE INTENSITY |
|---|---|
| 14.8 | 20.2 |
| 15.7 | 46.7 |
| 16.1 | 22.0 |
| 16.7 | 42.4 |
| 17.2 | 46.6 |
| 17.5 | 22.8 |
| 19.5 | 47.7 |
| 20.2 | 11.0 |
| 20.7 | 26.8 |
| 21.8 | 11.4 |
| 22.6 | 33.5 |
| 23.2 | 29.2 |
| 24.2 | 27.6 |

The PXRD pattern corresponding to the data reported in Table 8-M is graphically shown in FIG. 2-M.

TABLE 8-N

PXRD Peak Listing
Monohydrochloride Salt, Crystalline Form III

| PEAK POSITION (°2Θ) | RELATIVE INTENSITY |
|---|---|
| 6.7 | 79.6 |
| 8.5 | 27.4 |
| 10.0 | 3.6 |
| 11.2 | 6.9 |
| 12.9 | 4.4 |
| 15.7 | 25.1 |
| 16.1 | 4.7 |
| 17.1 | 12.9 |
| 19.3 | 10.0 |
| 20.1 | 6.0 |
| 20.7 | 23.3 |
| 22.0 | 80.2 |

The PXRD pattern corresponding to the data reported in Table 8-N is graphically shown in FIG. 2-N.

Example 9

Unit Cell Parameters

Unit cell parameters were determined and are reported below in Tables 9-A, 9-B, and 9-C for the hemi-sulfate salt (1:1 stoichiometry), monohydrate; the n-butylamine salt (1:1 stoichiometry), anhydrate; and the S-mandelate salt (1:1 stoichiometry), anhydrate, respectively.

Single crystal X-ray diffraction data were collected using a Bruker Apex II diffractometer (Bruker AXS, Madison, Wis.) equipped with an Apex II CCD area detector. The diffractometer was operated with a molybdenum anode tube (2.0 kW fine focus) at 50 kV and 40 mA. An incident beam silicon monochromator provided Mo-Kα1 monochromatic radiation. The data were collected under a stream of cold nitrogen gas at 100K using a Kryoflex low temperature device (Bruker AXS, Madison, Wis.). The beam diameter for data collection was 5 mm and the detector distance was 6 cm. The alignment of the goniometer was checked using a spherical 2-Dimethylsufuranylidene-1,3-indanedione (YLID) crystal. The instrument was computer controlled using the BIS and Apex 2 software programs (Bruker AXS, Madison, Wis.). The data were analyzed using Apex 2 software (Version 2011.2-0, Bruker AXS, Madison, Wis.).

TABLE 9-A

Unit Cell Parameters
Hemi-Sulfate Salt (1:1 Stoichiometry), Monohydrate

| Lattice Type | Monoclinic |
|---|---|
| Space Group | C2 |
| a (Å) | 32.47 |
| b (Å) | 5.628 |
| c (Å) | 15.891 |
| α (°) | 90 |
| β (°) | 97.449 |
| γ (°) | 90 |
| Volume (Å$^3$) | 2879.43 |
| Z | 4 |

TABLE 9-B

Unit Cell Parameters
n-Butylamine Salt (1:1 Stoichiometry), Anhydrate

| Lattice Type | Orthorhombic |
|---|---|
| Space Group | P2$_1$2$_1$2$_1$ |
| a (Å) | 6.437 |
| b (Å) | 22.601 |
| c (Å) | 23.324 |
| α (°) | 90 |
| β (°) | 90 |
| γ (°) | 90 |
| Volume (Å$^3$) | 3393.24 |
| Z | 4 |

TABLE 9-C

Unit Cell Parameters
S-Mandelate Salt (1:1 Stoichiometry), Anhydrate

| Lattice Type | Orthorhombic |
|---|---|
| Space Group | P 212121 |
| a (Å) | 9.954(2) |
| b (Å) | 11.049(2) |
| c (Å) | 30.861(6) |
| α (°) | 90.00 |
| β (°) | 90.00 |
| γ (°) | 90.00 |
| Volume (Å$^3$) | 3394 (1) |
| Z | 4 |

Unless otherwise indicated, in each Example below: (a) the atrasentan parent tested was the hemi-hydrate, (b) the atrasentan hydrochloride salt tested was the crystalline form II of the monohydrochloride salt, and (c) the atrasentan mandelate salt tested was the anhydrate of the S-mandelate salt (1:1 stoichiometry).

Example 10

Bulk Density

A study is conducted to evaluate the bulk density, tap density, and flow properties of atrasentan parent, atrasentan mandelate salt, and atrasentan hydrochloride salt.

A. General Methods

Bulk and tap density are measured following United States Pharmacopeia and National Formulary guidelines (USP <616>). Approximately 60 mL of each sample is added into a 100 mL graduated cylinder. The powder is carefully leveled without compacting, and the volume is read directly from the cylinder and used to calculate the bulk density according to the relationship: mass/volume. The cylinder containing the powder sample is then mechanically tapped using a VanKel Tap Density Tester (Model 50-1200, Varian, Inc., Palo Alto, Calif.) until there is no change in volume. The volume of the sample is then read and used in the calculation of tap density.

Flow properties of each sample are characterized using a Schulze ring shear tester RST-XS (Dietmar Schulze Schüttgutmesstechnik, Wolfenbüttel, Germany). A standard annular cell of a cross-sectional area of 24 cm$^2$ and a volume of 30 cm$^3$ is used to measure the yield loci. All experiments are performed at 23±2° C. and 33±2% relative humidity to minimize the effects of temperature and moisture on flow properties. During each measurement, the powder is first pre-sheared under a pre-consolidation stress until a steady-state is reached. The pre-sheared powder is then subjected to shear under a normal stress. Thus one shear point of the yield locus, a plot of shear stress at failure as a function of the normal stress, is obtained. To measure another shear point of the yield locus, the sample is then pre-sheared again under the same pre-consolidation stress and sheared to failure under a subsequently increased normal stress. A complete yield locus is then plotted through all measured shear points.

In this study, the procedure is conducted in triplicates with applying pre-consolidation stresses of 1 kPa and four normal stress levels equally spaced between 20 to 60% of the pre-consolidation stress. From each yield locus, major principle stress ($\sigma_1$) and unconfined yield strength ($f_c$) are derived by drawing two critical Mohr stress circles with the software RST-CONTROL 95 (Dietmar Schulze Schüttgutmesstechnik, Wolfenbüttel, Germany). The major principle stress ($\sigma_1$) results from the Mohr stress circle which is tangential to the yield locus and intersects at the point of normal and shear stresses at steady state flow. The unconfined yield strength ($f_c$) results from the Mohr stress circle which is tangential to the yield locus and runs through the origin. Flow function coefficient (FFC=$\sigma_1/f_c$) is used to characterize the flow of a powder.

B. Bulk Density and Tap Density Measurement

Bulk density and tap density were measured for samples of the following materials: (i) unmilled atrasentan hydrochloride salt having the morphology and particle size distribution listed below in Table 10; and (ii) unmilled atrasentan mandelate salt having the morphology and particle size distribution listed below in Table 10. Each sample had a moisture content less than 2% by weight at 80% relative humidity. Bulk density was measured in accordance with Bulk Density, Method I of United States Pharmacopeia and National Formulary Guidelines (USP <616>) except that a 100 mL cylinder was filled with the sample for the testing. Tap density was measured in accordance with Tapped Density, Method I of United States Pharmacopeia and National Formulary guidelines (USP <616>) except that a 100 mL cylinder was filled with the sample for the testing. Results are reported below in Table 10.

TABLE 10

Bulk Density and Tap Density

| SALT | | HYDROCHLORIDE | MANDELATE |
|---|---|---|---|
| MORPHOLOGY | | Needle | Prismatic |
| DESCRIPTION | | Unmilled | Unmilled |
| PARTICLE SIZE | D10 (μm) | 6.0 | 16 |
| DISTRIBUTION | D50 (μm) | 20 | 49 |
| | D90 (μm) | 86 | 141 |
| BULK DENSITY (g/mL) | | 0.11 | 0.25 |
| TAP DENSITY (g/mL) | | 0.20 | 0.40 |

Example 11

Oxidative Stability

A study was conducted to evaluate the oxidative stability of atrasentan parent, atrasentan mandelate salt, and atrasentan hydrochloride salt.

About 1 mg of each solid was placed in a 4 mL glass vial and about 10 mg of urea-H$_2$O$_2$ co-crystal was placed in another 4 mL vial. The two vials then were connected by a connector (Kontes connector, 13-425X13-425, apt NO 747205-1313) and left in an oven at 40° C. for seven days. Blank samples were prepared by placing about 1 mg of each compound in a 4 mL vial and then storing the vial in a freezer at about −20° C. for the same period of time. The oven samples and freezer blanks were analyzed at the same time by HPLC. The HPLC conditions are summarized in Table 11-A below. The measured data are reported in Table 11-B below and the normalized data from Table 11-B are shown in a bar chart in FIG. 3.

TABLE 11-A

HPLC Conditions

| HPLC METHOD | |
|---|---|
| Column | YMC, 150 mm × 4.6 mm, paced with spherical 3 μm C4 particles, 120 Å pore size |
| Flow rate | 1 ml/min |
| Column temperature | 17° C. |
| injection volume | 20 μl |
| Detector wavelength | 234 nm |
| GRADIENT | |
| Mobile phase A | pH 2.0 Perchloric acid solution: Adjust pH of Milli-Q water to pH 2.0 using perchloric acid |
| Mobile phase B | Acetonitrile |

| Time (minutes) | Perchloric acid solution (%) | Acetonitrile (%) |
|---|---|---|
| 0 | 70 | 30 |
| 5 | 70 | 30 |
| 45 | 45 | 55 |
| 75 | 45 | 55 |
| 77 | 70 | 30 |
| 90 | 70 | 30 |

TABLE 11-B

Oxidative Stability Data

| SAMPLE | CONCEN. (mg/mL) | RECOVERED WEIGHT (mg) | INITIAL WEIGHT (mg) | RECOVERED (%) | AVERAGE (%) | STD | AVERAGE % (NORMALIZED) | SAMPLE RECOVERY PROPORTION (%) |
|---|---|---|---|---|---|---|---|---|
| Parent Blank 1 | 29.126 | 1.165 | 1.13 | 103.10 | 102.26 | 0.84 | 89.56 | |
| Parent Blank 2 | 27.867 | 1.115 | 1.09 | 102.26 | | | | |

TABLE 11-B-continued

Oxidative Stability Data

| SAMPLE | CONCEN. (mg/mL) | RECOVERED WEIGHT (mg) | INITIAL WEIGHT (mg) | RECOVERED (%) | AVERAGE (%) | STD | AVERAGE % (NORMALIZED) | SAMPLE RECOVERY PROPORTION (%) |
|---|---|---|---|---|---|---|---|---|
| Parent Blank 3 | 27.636 | 1.105 | 1.09 | 101.42 | | | | |
| Parent Sample 1 | 22.737 | 0.909 | 0.97 | 93.76 | 91.58 | 2.20 | | 91.69 |
| Parent Sample 2 | 21.760 | 0.870 | 0.95 | 91.62 | | | | 89.60 |
| Parent Sample 3 | 24.577 | 0.983 | 1.1 | 89.37 | | | | 87.39 |
| Hydrochloride Blank 1 | 26.127 | 1.045 | 1.08 | 96.77 | 96.09 | 0.60 | 89.48 | |
| Hydrochloride Blank 2 | 30.687 | 1.227 | 1.28 | 95.90 | | | | |
| Hydrochloride Blank 3 | 29.160 | 1.166 | 1.22 | 95.61 | | | | |
| Hydrochloride Sample 1 | 21.029 | 0.841 | 0.96 | 87.62 | 85.98 | 2.49 | | 91.18 |
| Hydrochloride Sample 2 | 24.637 | 0.985 | 1.13 | 87.21 | | | | 90.76 |
| Hydrochloride Sample 3 | 22.856 | 0.914 | 1.1 | 83.11 | | | | 86.49 |
| Mandelate Blank 1 | 22.676 | 0.907 | 1.07 | 84.77 | 80.14 | 4.18 | 99.30 | |
| Mandelate Blank 2 | 20.545 | 0.822 | 1.04 | 79.02 | | | | |
| Mandelate Blank 3 | 19.349 | 0.774 | 1.01 | 76.63 | | | | |
| Mandelate Sample 1 | 22.248 | 0.890 | 1.08 | 82.40 | 79.58 | 3.50 | | 102.82 |
| Mandelate Sample 2 | 20.975 | 0.839 | 1.04 | 80.67 | | | | 100.66 |
| Mandelate Sample 3 | 22.856 | 0.914 | 1.1 | 83.11 | | | | 94.41 |

The oxidative stability data reported in Table 11-B were further evaluated by ANOVA analysis. The ANOVA results are reported in Table 11-C below.

TABLE 11-C

ANOVA Analysis

| | ESTIMATE | STANDARD ERROR | t VALUE | Pr (> | t |) |
|---|---|---|---|---|
| (Intercept) | 0.99297 | 0.01839 | 54.008 | 2.71E−09 |
| Hydrochloride Salt-Mandelate Salt | −0.09822 | 0.02600 | −3.777 | 0.00921 |
| Atrasentan Parent-Mandelate Salt | −0.09738 | 0.02600 | −3.745 | 0.00956 |

The data show that the mandelate salt had a statistically significantly higher sample recovery proportion than the hydrochloride salt and atrasentan parent and, therefore, had greater oxidative stability than the atrasentan parent and hydrochloride salt.

Example 12

Intrinsic Dissolution Rate (Function of pH)

A study was conducted to evaluate the intrinsic dissolution rate as a function of pH for two different crystal forms having prismatic morphology (atrasentan parent and atrasentan mandelate salt).

Figure 4:
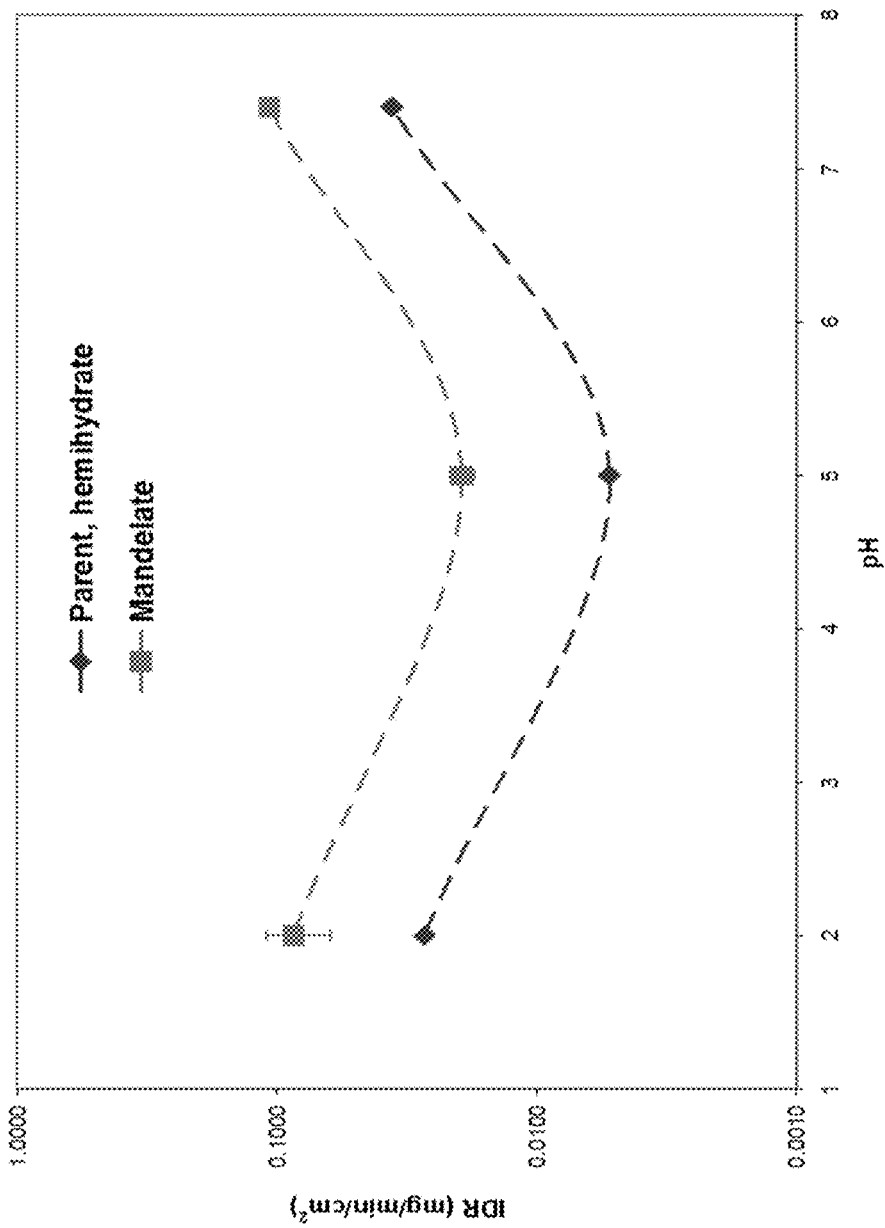
FIG. 4 is a graph illustrating the intrinsic dissolution rate as a function of pH for atrasentan S-mandelate (1:1 stoichiometry), anhydrate, and atrasentan parent, hemihydrate.

About 100 mg of the sample tested was prepared by compressing the sample in a stainless steel die under 1100 pounds force with a dwell time of one minute to form a pellet. The die (diameter: 0.373 inch, area: 0.704 cm$^2$) containing the pellet was submerged in 250 mL of a phosphate buffer dissolution test medium having a pH of 2.0, 5.0, or 7.4. The medium was stirred by a paddle at 50 rpm and maintained at 37° C. To measure the concentration of the sample material in the medium, a fiber optic dip probe (μDiss Profile, pION Inc) was used to monitor the UV absorbance as a function of time. The measured data are reported in Table 12-A below and are shown graphically in FIG. 4.

TABLE 12-A

Intrinsic Dissolution Rate ("IDR")

| pH | MANDELATE IDR** (mg/min/cm$^2$) | PARENT IDR** (mg/min/cm$^2$) |
|---|---|---|
| 2.0 | $1.0 \times 10^{-1}$ $6.9 \times 10^{-2}$ | $2.7 \times 10^{-2}$ (n = 1) |
| 5.0 | $2.1 \times 10^{-2}$ $1.8 \times 10^{-2}$ | $5.1 \times 10^{-3}$ $5.4 \times 10^{-3}$ |
| 7.4 | $1.1 \times 10^{-1}$ $1.0 \times 10^{-1}$ | $3.6 \times 10^{-2}$ (n = 1) |

**Data reported for two runs (i.e., n = 2) unless otherwise indicated.

The intrinsic dissolution data reported in Table 12-A were further evaluated using a paired t-test analysis that provided the following results:

t=2.6645 df=3 p-value=0.03802 (<0.05).

The S-mandelate salt exhibited a statistically greater intrinsic dissolution rate than the corresponding atrasentan parent.

Example 13

Intrinsic Dissolution Rate (Function of [Cl⁻])

A study was conducted to evaluate the intrinsic dissolution rate as a function of chloride ion concentration ([Cl⁻]) for atrasentan mandelate salt and atrasentan hydrochloride salt.

Figure 5:
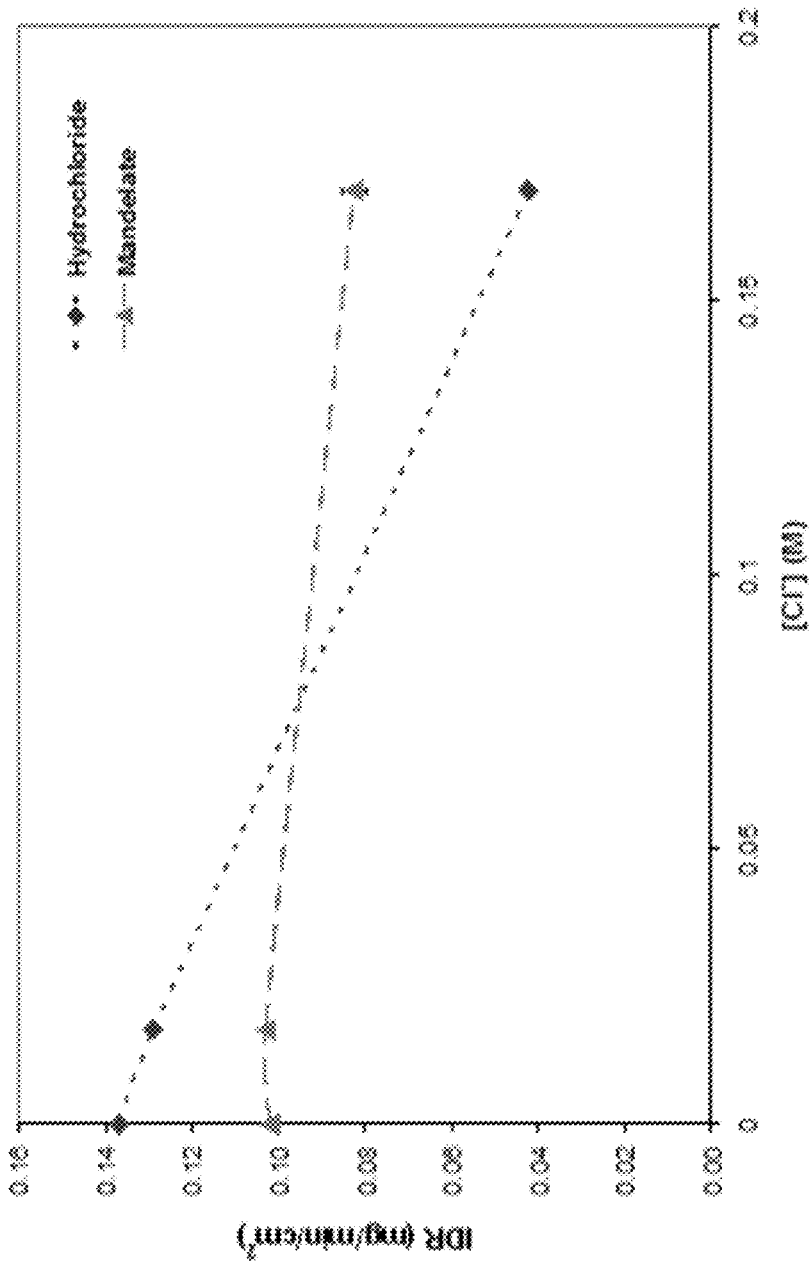
FIG. 5 is a graph illustrating the intrinsic dissolution rate as a function of chloride ion concentration for atrasentan S-mandelate (1:1 stoichiometry), anhydrate, and atrasentan monohydrochloride, crystalline Form II.

About 100 mg of the sample tested was prepared by compressing the sample in a stainless steel die under 1100 pounds force with a dwell time of one minute to form a pellet. The die (diameter: 0.373 inch, area: 0.704 cm$^2$) containing the pellet was submerged in 250 mL of a phosphate buffer dissolution test medium having a pH of 2.0 and a chloride ion concentration of 0 M, 0.017 M, or 0.17 M. The medium was stirred by a paddle at 50 rpm and maintained at 37° C. To measure the concentration of the sample material in test medium, a fiber optic dip probe (μDiss Profile, pION Inc) was used to monitor the UV absorbance as a function of time. The measured data are reported in Table 13-A below and are shown graphically in FIG. 5.

TABLE 13-A

| | Intrinsic Dissolution Rate ("IDR") | |
|---|---|---|
| [Cl⁻] (M) | HYDROCHLORIDE IDR (mg/min/cm²) | MANDELATE IDR (mg/min/cm²) |
| 0.17 | $4.2 \times 10^{-2}$ (n = 1) | $8.3 \times 10^{-2}$ (n = 3)** |
| 0.017 | $1.3 \times 10^{-1}$ (n = 1) | $1.0 \times 10^{-1}$ (n = 1) |
| 0.0 | $1.4 \times 10^{-1}$ (n = 1) | $1.0 \times 10^{-1}$ (n = 1) |

**Measured values were $8.2 \times 10^{-2}$, $8.6 \times 10^{-2}$, and $8.0 \times 10^{-2}$.

The intrinsic dissolution data reported in Table 13-A were further evaluated using linear regression analysis. The linear regression analysis results are reported in Table 13-B.

TABLE 13-B

| Linear Regression Analysis | |
|---|---|
| MANDELATE SALT MODEL: IDR = a1 + b1 × [Cl⁻] | HYDROCHLORIDE SALT MODEL: IDR = a2 + b2 × [Cl⁻] |
| a1 = 0.103458 | a2 = 0.1377269 |
| b1 = −0.122241 | b2 = −0.5608597 |
| p-value = 0.00383 | p-value = 0.00934 |
| Slope difference (b1-b2) = 0.4386 (p-value < 0.0001) | |

The S-mandelate salt exhibited a statistically smaller slope than the hydrochloride salt in the linear regression analysis which indicates the intrinsic dissolution rate of the mandelate salt is less sensitive to chloride ion concentration than the intrinsic dissolution rate of the hydrochloride salt.

Example 14

Corrosivity (Suspension at 50° C.)

A study was conducted to evaluate the corrosivity of atrasentan mandelate salt and atrasentan hydrochloride salt. The test was conducted in accordance with the American Society for Testing and Materials (ASTM) Practice G31-72 "Standard Practice for Laboratory Immersion Corrosion Testing of Metals" (Reapproved 2004) (see Annual Book of ASTM (American Society for Testing and Materials) Standards, Vol. 03.02, 2004).

Six stainless steel 316LW (welded) coupons were hand polished and stamped with identifying marks. They were then washed in an ultrasonic bath with detergent for fifteen minutes, rinsed with tap water, rinsed with acetone, and then dried. The dimensions of each coupon were measured using a digital caliper with accuracy of ±0.05 mm. The coupons were weighed with an analytical balance to an accuracy of ±0.1 mg.

Three of the coupons were completely submerged in the liquid phase of an atrasentan mandelate salt suspension (an aqueous suspension containing 9.545% atrasentan mandelate salt by weight and 8.8% HPMC E5 by weight). The remaining three coupons were completely submerged in the liquid phase of an atrasentan monohydrochloride salt suspension (an aqueous suspension containing 7.215% atrasentan monohydrochloride salt by weight and 8.8% HPMC E5 by weight). The suspensions were agitated using a magnetic stir bar and maintained at 50° C. After days 1, 5, and 15, one coupon and 5 mL of the exposed suspension were removed from each suspension. The appearance of the removed coupons was observed and recorded. The coupons then were washed in an ultrasonic bath with detergent for fifteen minutes, rinsed with tap water, rinsed with acetone, dried, and weighed.

The corrosion rate (inches per year, "IPY") was calculated using the following formula (see Annual Book of ASTM (American Society for Testing and Materials) Standards, Vol. 03.02, 2004):

$$\text{Corrosion Rate} = \frac{3450 \times \Delta W}{A \times t \times \rho}$$

where:

$\Delta W$ = weight loss (g)

$A$ = surface area of coupon (cm²)

$t$ = duration of experiment (hours)

$\rho$ = density of coupon (g/cm³)

The corrosivity test conditions and results for the two suspensions are reported in Tables 14-A and 14-B below. Table 14-C below (reproduced from Corrosion Resistance Tables, Fourth Edition, Revised and Expanded, edited by Philip A. Schweitzer, 1995) provides a general guide for interpreting the corrosion test results for metal specimens at the testing temperature.

TABLE 14-A

| Corrosion Results for Mandelate Salt Suspension | | | |
|---|---|---|---|
| | COUPON B | COUPON A | COUPON C |
| Test Duration (h) | 24 | 120 | 360 |
| Length (cm) | 3.716 | 3.771 | 3.771 |
| Width (cm) | 1.585 | 1.616 | 1.618 |
| Thickness (cm) | 0.292 | 0.306 | 0.303 |
| Surface Area (cm²) | 14.88 | 15.48 | 15.47 |
| Starting Weight (g) | 12.9573 | 14.0885 | 13.5392 |
| Final Weight (g) | 12.957 | 14.0881 | 13.5387 |
| Weight Change (g) | 0.0003 | 0.0004 | 0.0005 |
| Corrosion Rate (IPY) | $3.63 \times 10^{-4}$ | $9.31 \times 10^{-5}$ | $3.88 \times 10^{-5}$ |
| Appearance | Unchanged | Unchanged | Unchanged |

TABLE 14-B

| Corrosion Results for Hydrochloride Salt Suspension | | | |
|---|---|---|---|
| | COUPON F | COUPON E | COUPON D |
| Test Duration (h) | 24 | 120 | 360 |
| Length (cm) | 3.669 | 3.718 | 3.769 |
| Width (cm) | 1.59 | 1.596 | 1.597 |
| Thickness (cm) | 0.296 | 0.298 | 0.297 |
| Surface Area (cm²) | 14.78 | 15.04 | 15.23 |
| Starting Weight (g) | 12.8682 | 12.9074 | 13.4665 |
| Final Weight (g) | 12.868 | 12.9073 | 13.4653 |
| Weight Change (g) | 0.0002 | 0.0001 | 0.0012 |
| Corrosion Rate (IPY) | $2.44 \times 10^{-4}$ | $2.40 \times 10^{-5}$ | $9.47 \times 10^{-5}$ |
| Appearance | Unchanged | Unchanged | Unchanged |

TABLE 14-C

| Corrosion Guide | |
|---|---|
| CORROSION RESISTIVITY | CORROSION RATE |
| Excellent | $\leq 2.0 \times 10^{-3}$ inch/year |
| Good | $\leq 2.0 \times 10^{-2}$ inch/year |
| Satisfactory | $\leq 5.0 \times 10^{-2}$ inch/year |
| Unsatisfactory | $\geq 5.0 \times 10^{-2}$ inch/year |

Example 15

Corrosivity (Suspension at 75° C.)

A second study was conducted to evaluate the corrosivity of atrasentan mandelate salt and atrasentan hydrochloride salt. The test was conducted in accordance with Annual Book of ASTM (American Society for Testing and Materials) Standards, Vol. 03.02, 2004.

Six stainless steel 316LW (welded) coupons were hand polished and stamped with identifying marks. They were then washed in an ultrasonic bath with detergent for fifteen minutes, rinsed with tap water, rinsed with acetone, and then dried. The dimensions of each coupon were measured using a digital caliper with accuracy of ±0.05 mm. The coupons were weighed with an analytical balance to an accuracy of ±0.1 mg.

Three of the coupons were completely submerged in the liquid phase of an atrasentan mandelate salt suspension and the remaining three coupons were completely submerged in the liquid phase of an atrasentan monohydrochloride salt suspension. The compositions of the salt suspensions are described in Tables 15-A and 15-B below.

TABLE 15-A

Composition of Mandelate Salt Suspension

| SUSPENSION COMPONENT | ACTUAL WEIGHT (g) | WEIGHT PERCENT |
|---|---|---|
| Atrasentan Mandelate (662.8 g/mol) | 5.7125 | 27.53 |
| HPMC E5 (8.8% solution added) | 0.3555 | 1.71 |
| Lactose MH regular | 6.0085 | 28.96 |
| Water | 8.6745 | 41.80 |
| Total | 20.751 | 100.00 |

TABLE 15-B

Composition of Hydrochloride Salt Suspension

| SUSPENSION COMPONENT | ACTUAL WEIGHT (g) | WEIGHT PERCENT |
|---|---|---|
| Atrasentan Monohydrochloride (547.1 g/mol) | 4.3089 | 18.24 |
| HPMC E5 (8.8% solution added) | 0.35728 | 1.51 |
| Lactose MH regular | 6.043 | 25.58 |
| Water | 12.91272 | 54.66 |
| Total | 23.6219 | 100.00 |

The suspensions were placed in an oven and maintained at 75° C. One coupon was removed from each suspension each week. The appearance of the removed coupons was observed and recorded. The coupons then were washed in an ultrasonic bath with detergent for fifteen minutes, rinsed with tap water, rinsed with acetone, dried, and weighed.

The corrosion rate was calculated in the same manner as discussed in Example 14. The corrosivity test conditions and results for the two suspensions are summarized in Tables 15-C and 15-D.

TABLE 15-C

Corrosion Results for Mandelate Salt Suspension

| TEST DETAILS | | | |
|---|---|---|---|
| Coupon Type | SS316LW | | |
| Density (g/cm³) | 7.98 | | |
| COUPON DETAILS | | | |
| | F | E | D |
| Location | | | |
| Length (cm) | 3.768 | 3.71 | 3.715 |
| Width (cm) | 1.588 | 1.581 | 1.577 |
| Thickness (cm) | 0.312 | 0.29 | 0.294 |
| Starting weight (g) | 13.8479 | 12.8965 | 12.7577 |
| Final weight (g) | 13.8478 | 12.8961 | 12.7565 |
| Appearance | Unchanged | Unchanged | Unchanged |
| TEST RESULTS | | | |
| Time (hours) | 169.25 | 337.92 | 570.75 |
| Surface Area (cm²) | 15.31 | 14.80 | 14.83 |
| Weight Change (g) | −0.0001 | −0.0004 | −0.0012 |
| Corrosion Rate (IPY) | $1.67 \times 10^{-5}$ | $3.46 \times 10^{-5}$ | $6.13 \times 10^{-5}$ |

TABLE 15-D

Corrosion Results for Hydrochloride Salt Suspension

| TEST DETAILS | | | |
|---|---|---|---|
| Coupon Type | SS316LW | | |
| Density (g/cm³) | 7.98 | | |
| COUPON DETAILS | | | |
| | A | C | B |
| Location | | | |
| Length (cm) | 3.748 | 3.639 | 3.726 |
| Width (cm) | 1.599 | 1.586 | 1.579 |
| Thickness (cm) | 0.308 | 0.301 | 0.293 |
| Starting weight (g) | 13.9433 | 12.8431 | 12.8826 |
| Final weight (g) | 13.9424 | 12.8405 | 12.8776 |
| Appearance | Unchanged | Unchanged | Etching Visible on Weld |
| TEST RESULTS | | | |
| Time (hours) | 169.25 | 337.92 | 570.75 |
| Surface Area (cm²) | 15.28 | 14.69 | 14.88 |
| Weight Change (g) | −0.0009 | −0.0026 | −0.0050 |
| Corrosion Rate (IPY) | $1.50 \times 10^{-4}$ | $2.26 \times 10^{-4}$ | $2.55 \times 10^{-4}$ |

Example 16

Moisture Sorption Isotherm

A study was conducted to evaluate the moisture sorption isotherms of atrasentan hemi-sulfate salt (1:1 stoichiometry), monohydrate, and atrasentan S-mandelate salt (1:1 stoichiometry), anhydrate. A sample (about 5 mg to about 20 mg) of the powder to be tested was loaded onto the tared pan of a DVS Advantage dynamic gravimetric water sorption analyzer (Surface Measurement Systems Ltd, Alperton, United Kingdom). The moisture sorption isotherm for each sample was collected at 10% relative humidity intervals as the relative humidity was adjusted in the following manner: (a) 0% to 90% to 0% to 90% to 40% for the hemi-sulfate salt, and (b) 0% to 90% to 0% for the S-mandelate salt. For each step, the dm/dt criteria were 0.001% over 5 minutes with a minimum dm/dt time of 30 minutes and a maximum dm/dt of 120 minutes. Data was collected isothermally at 25° C. with a nitrogen flow rate of 200 cm²/minute. The sample was maintained at 30% relative humidity and analyzed by PXRD. The moisture sorption isotherms generated for the hemi-sulfate and S-mandelate salt samples are shown in FIG. 6-A and FIG. 6-B, respectively. The hemi-sulfate salt exhibited partial conversion from the hydrate form to the anhydrate form as the relative humidity decreased below 10%.

Example 17

Differential Scanning Calorimetry

Atrasentan hemi-sulfate salt (1:1 stoichiometry), monohydrate, and atrasentan S-mandelate salt (1:1 stoichiometry), anhydrate, were analyzed by differential scanning calorimetry ("DSC"). A differential scanning calorimeter (Q-2000, TA Instruments, New Castle, Del.) equipped with Universal Analysis 2000 software (Version 4.5A, TA Instruments, New Castle, Del.) was used to determine the DSC thermal traces. The temperature axis was calibrated with biphenyl, indium, and tin standards. The cell constant was calibrated with indium. Unless otherwise stated, the sample (2 to 5 mg) was encapsulated in a ventilated aluminum pan, and heated at a rate of 10° C./minute under a nitrogen gas flow of 50 mL/minute during the study. The DSC curves generated for the hemi-sulfate and S-mandelate salt samples are shown in FIG. 7-A and FIG. 7-B, respectively.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

We claim:

1. A crystalline atrasentan S-mandelate anhydrous salt wherein the molar ratio of atrasentan to S-mandelate is about 1:1.

2. The salt of claim 1, wherein the salt has an X-ray powder diffraction pattern comprising peaks at 5.5±0.2, 9.7±0.2, and 19.4±0.2 degrees two theta when measured at about 25° C. with monochromatic Kα1 radiation.

3. The salt of claim 1, wherein the salt has an orthorhombic lattice type.

4. A pharmaceutical composition comprising the salt of claim 1 and a pharmaceutically-acceptable carrier.

5. The composition of claim 4, wherein the composition comprises from about 0.25 mg to about 1.25 mg of the salt on an atrasentan parent equivalent weight basis.

6. A method of treating chronic kidney disease, comprising administering a therapeutically effective amount of the salt of claim 1 to a human subject susceptible to or suffering from chronic kidney disease.

7. The method of claim 6, wherein the amount of the salt administered is from about 0.25 mg daily to about 1.25 mg daily on an atrasentan parent equivalent weight basis.

8. A method of treating nephropathy, comprising administering a therapeutically effective amount of the salt of claim 1 to a human subject susceptible to or suffering from nephropathy.

9. The method of claim 8, wherein the amount of the salt administered is from about 0.25 mg daily to about 1.25 mg daily on an atrasentan parent equivalent weight basis.

10. The method of claim 8, wherein the method reduces the urinary-albumin-to-creatinine ratio in the subject.

11. The method of claim 8, wherein the method reduces the rate of increase in serum creatinine concentration in the subject.

* * * * *